US009532897B2

(12) United States Patent
Huber et al.

(10) Patent No.: US 9,532,897 B2
(45) Date of Patent: *Jan. 3, 2017

(54) DEVICES THAT TRAIN VOICE PATTERNS AND METHODS THEREOF

(71) Applicant: Purdue Research Foundation, West Lafayette, IN (US)

(72) Inventors: Jessica E. Huber, Lafayette, IN (US); Scott Kepner, West Lafayette, IN (US); Derek Tully, Indianapolis, IN (US); James Thomas Jones, Brookston, IN (US); Kirk Solon Foster, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 219 days.

This patent is subject to a terminal disclaimer.

(21) Appl. No.: 14/332,679

(22) Filed: Jul. 16, 2014

(65) Prior Publication Data
US 2014/0330557 A1  Nov. 6, 2014

Related U.S. Application Data

(63) Continuation-in-part of application No. 14/266,289, filed on Apr. 30, 2014, now Pat. No. 9,381,110, which
(Continued)

(51) Int. Cl.
*H04R 25/02* (2006.01)
*A61F 5/58* (2006.01)
(Continued)

(52) U.S. Cl.
CPC ............... *A61F 5/58* (2013.01); *G09B 19/04* (2013.01); *G09B 21/00* (2013.01); *H04R 1/1091* (2013.01);
(Continued)

(58) Field of Classification Search
CPC ............... A61F 5/58; G10L 2021/0575; G10L 2021/03646; H04R 25/00–25/75; G09B 19/04
See application file for complete search history.

(56) References Cited

U.S. PATENT DOCUMENTS 3,349,179 A  10/1967 Klein
3,566,858 A   3/1971 Larson et al.
(Continued)

FOREIGN PATENT DOCUMENTS

EP    2051241 A1    4/2009

OTHER PUBLICATIONS

Ho A K et al. Speech volume regulation in Parkinson's disease: effects of implicity cues and explicit instructions. Neuropsychologia 37, p. 1453-1460, 1999.*
(Continued)

*Primary Examiner* — Catherine B Kuhlman
(74) *Attorney, Agent, or Firm* — LeClairRyan, a Professional Corporation

(57) ABSTRACT

A voice enhancement device including an earpiece configured to be positioned in an ear canal of a user. A microcontroller is operatively coupled to the earpiece. The microcontroller is configured to selectively provide at least multitalker babble. An accelerometer is located within the earpiece and operatively coupled to the microcontroller. The accelerometer is configured to detect speech by the user and communicate with the microcontroller to provide the multitalker babble to the earpiece during the detected speech by the user. A method of making the voice enhancement device, and a method for increasing vocal loudness in a patient using the voice enhancement device are also disclosed.

27 Claims, 19 Drawing Sheets

Related U.S. Application Data is a continuation of application No. 13/835,802, filed on Mar. 15, 2013, now abandoned, which is a continuation-in-part of application No. PCT/US2010/045568, filed on Aug. 16, 2010, application No. 14/332,679, which is a continuation-in-part of application No. 13/398,399, filed on Feb. 16, 2012, now abandoned, which is a continuation-in-part of application No. PCT/US2010/045568, application No. 14/332,679, which is a continuation-in-part of application No. PCT/US2012/026033, filed on Feb. 22, 2012, which is a continuation of application No. 13/398,399, said application No. PCT/US2012/026033 is a continuation-in-part of application No. PCT/US2010/045568, filed on Aug. 16, 2010.

(60) Provisional application No. 61/234,401, filed on Aug. 17, 2009, provisional application No. 61/445,780, filed on Feb. 23, 2011.

(51) Int. Cl.

| | | |
|---|---|---|
| G09B 19/04 | (2006.01) | |
| G09B 21/00 | (2006.01) | |
| H04R 3/00 | (2006.01) | |
| G10L 21/0364 | (2013.01) | |
| G10L 21/057 | (2013.01) | |
| H04R 1/10 | (2006.01) | |

(52) U.S. Cl.
CPC ....... *H04R 3/00* (2013.01); *G10L 2021/03646* (2013.01); *G10L 2021/0575* (2013.01); *H04R 1/1016* (2013.01); *H04R 2420/07* (2013.01); *H04R 2420/09* (2013.01); *H04R 2460/13* (2013.01)

(56) References Cited

U.S. PATENT DOCUMENTS

| | | | |
|---|---|---|---|
| 3,773,032 A | | 11/1973 | Donovan et al. |
| 3,881,059 A | | 4/1975 | Stewart |
| 4,143,648 A | * | 3/1979 | Cohen ................. A61F 5/58 128/905 |
| 4,335,276 A | | 6/1982 | Bull et al. |
| 4,464,119 A | * | 8/1984 | Vildgrube .............. G09B 19/04 381/56 |
| 4,784,115 A | | 11/1988 | Webster |
| 4,802,484 A | | 2/1989 | Friedman et al. |
| 5,659,620 A | | 8/1997 | Kuhlman |
| 5,940,798 A | | 8/1999 | Houde |
| 5,961,443 A | | 10/1999 | Rastatter et al. |
| 6,231,500 B1 | | 5/2001 | Kehoe |
| 6,754,632 B1 | * | 6/2004 | Kalinowski ............ A61F 5/58 600/23 |
| 7,181,024 B1 | | 2/2007 | Oba et al. |
| 7,260,209 B2 | | 8/2007 | Harvey et al. |
| 7,292,985 B2 | | 11/2007 | Jiang et al. |
| 7,591,779 B2 | | 9/2009 | Kalinowski et al. |
| 7,822,712 B1 | | 10/2010 | Robinson et al. |
| 8,257,243 B2 | | 9/2012 | Rastatter et al. |
| 8,275,624 B2 | | 9/2012 | Kehoe |
| 2002/0164013 A1 | * | 11/2002 | Carter ................... H04M 7/006 379/387.02 |
| 2003/0125096 A1 | * | 7/2003 | Boesen ............... H04M 1/0214 455/569.2 |
| 2003/0195588 A1 | | 10/2003 | Fischell et al. |
| 2006/0089522 A1 | | 4/2006 | Rastatter et al. |
| 2006/0126859 A1 | | 6/2006 | Elberling |
| 2007/0102525 A1 | | 5/2007 | Orr et al. |
| 2007/0190982 A1 | | 8/2007 | Le Faucheur |
| 2009/0264789 A1 | | 10/2009 | Molnar et al. |
| 2010/0100388 A1 | | 4/2010 | Kehoe |
| 2010/0280336 A1 | | 11/2010 | Giftakis et al. |

OTHER PUBLICATIONS

Winkworth A et al. Speech Breathing and the Lombard Effect. Journal of Speech, Language & Hearing Research 40(1), p. 159-169, 1997.*

Ohlsson et al., "A Voice Accumulator—Validation and Application," 32:451-457, Journal of Speech and Hearing Research (Jun. 1989).

Cheyne et al., "Development and Testing of a Portable Vocal Accumulator," 46:1457-1467, Journal of Speech, Language, and Hearing Research (Dec. 2003).

Popolo et al., "Adaptation of a Pocket PC for Use as a Wearable Voice Dosimeter," 48:780-791, Journal of Speech, Language, and Hearing Research (Aug. 2005).

Ho et al., "Speech Volume Regulation in Parkinson's Disease: Effects of Implicit Cues and Explicit Instructions," 37 (13)1453-1460, Neuropsychologia (Dec. 1999).

International Search Report and Written Opinion, 47 pages, dated Jun. 29, 2012 for International Application No. PCT/US2012/026033.

Pinto et al., "Treatments for Dysarthria in Parkinson's Disease," 3:547-556, The Lancet Neurology, [retrieved on Jun. 24, 2012]. Retrieved from the Internet at URL:htty://aune.lpl.univ.aix.fr/~fulltext/3022.pdf.

Lane et al., "The Lombard Sign and the Role of Hearing in Speech," 14:677-709, Journal of Speech and Hearing Research (Dec. 1971).

Adams et al., "Can the Lombard Effect be Used to Improve Low Voice Intensity in Parkinson's Disease?," 27:121-125, European Journal of Disorders of Communication (1992).

Levine et al., "Diagnosis and Treatment of Parkinson's Disease: A Systematic Review of the Literature [online]," 57:1-4, Evidence Report/Technology Assessment (Jun. 2003).

Quedas et al., "Lombard's Effect's Implication in Intensity, Fundamental Frequency and Stability on the Voice of Individual's with Parkinson's Disease," 73(5):675-683, Brazilian Journal of Otorhinolaryngology (Sep. 2007).

Sadagopan et al., "Effects on Loudness Cues on Respiration in Individuals with Parkinson's Disease," 22(5):651-659, Movement Disorders (Apr. 15, 2007).

Coutinho et al., "Voice and Speech of Individuals with Parkinson's Disease During amplification, Delay and Masking Situations," 21(3):219-224, Pro=Fono Revista de Atualizacao Cientifica, Brazil (Jul. 2009).

Johnson et al., "Nonpharmacological Management of Hypokinetic Dysarthia in Parkinson's Disease," 9(1):40-43, Geriatrics and Aging (Jan. 1, 2006).

Kiran et al., "Effect of Duration of Pitch-Shifted Feedback on Vocal Responses in Patients with Parkinson's Disease," 44:975-987 (Oct. 2001).

McCaffrey, "The Neuroscience on the Web Series: CMSD 642 Neuropathologies of Swallowing and Speech," [online] [Retrieved on May 16, 2012]. Retrieved on the Internet URL:http://csuchico.edu/~pmmccaffrey//syllabi/SPPA342/342UNIT14.html, 9 pp.

Rush University Medical Center, "Improve Speech Using an in the Ear Device in Parkinson's Disease (MJFFSpeech)," [online] Feb. 2008, pp. 1-4 [Retrieved on May 16, 2012]. Retrieved from the Internet URL:http://clinicaltrials.gov/ct/show/NCT00488657?order=1.

Venere et al., "New Technology Helps Parkinson's Patients Speak Louder," pp. 1-4, Purdue University News (Aug. 25, 2009).

International Search Report and Written Opinion, 9 pp., dated Oct. 27, 2010 for International Application No. PCT/US2010/045568.

Adams et al., "Effects of Multitalker Noise on Conversational Speech Intensity in Parkinson's Disease," 14(4):221-228, Journal of Medical Speech-Language Pathology (2006).

Adams et al., "Effects of Selected Practice and Feedback Variables on Speech Moto Learning," 8(4):215-220, Journal of Medical Speech-Language Pathology (2000).

Siegel et al., "Auditory Feedback in the Regulation of Voice," 56(5):1618-1624, Journal of Acoustical Society of America (Nov. 1974).

(56) References Cited

OTHER PUBLICATIONS

Pick, Jr., et al., "Inhibiting the Lombard Effect," 85(2):894-900, Journal of Acoustical Society of America (Feb. 1989).
Winkworth et al., "Speech Breathing and the Lombard Effect," 40:159-169, Journal of Speech, Language and Hearing Research, Sydney, Australia (Feb. 1997).
Indiana CTSI HUB—PDT program supports—Parkinson's device development.
Garnier et al., "Influence of Sound Immersion and Communicative Interaction on the Lombard Effect," 53:588-608, Journal of Speech, Language, and Hearing Research (Jun. 2010).
Wang et al., "Treating Festinating Speech With Altered Auditory Feedback in Parkinson's Disease: A Preliminary Report," 16(4):275-282, Journal of Medical Speech, Language, Pathology (2008).
Darling et al., "Changes to Articulatory Kinematics in Response to Loudness Cues in Individuals with Parkinson's Disease," 54:1247-1259, Journal of Speech, Language, and Hearing Research (Oct. 2011).
Svec et al., "Vocal Dosimetry: Theoretical and Practical Issues," AQL 2003 Hamburg; Proceeding Papers for the Conference Advances in Quantitative Laryngology, Voice and Speech Research edited by Schade et al., Published by IRB Vertag, Stuttgart, Germany (2003).
Aileen et al., "Speech Volume Regulation in Parkinson's Disease: Effects of Implicit Cues and Explicit Instructions," 37:1453-1460 Neuropsychologia (1999).
Adams et al., "Summary Feedback Schedules and Speech Motor Learning in Parkinson's Disease," 10(4):215-220, Journal of Medical Speech-Language Pathology (2002).

* cited by examiner

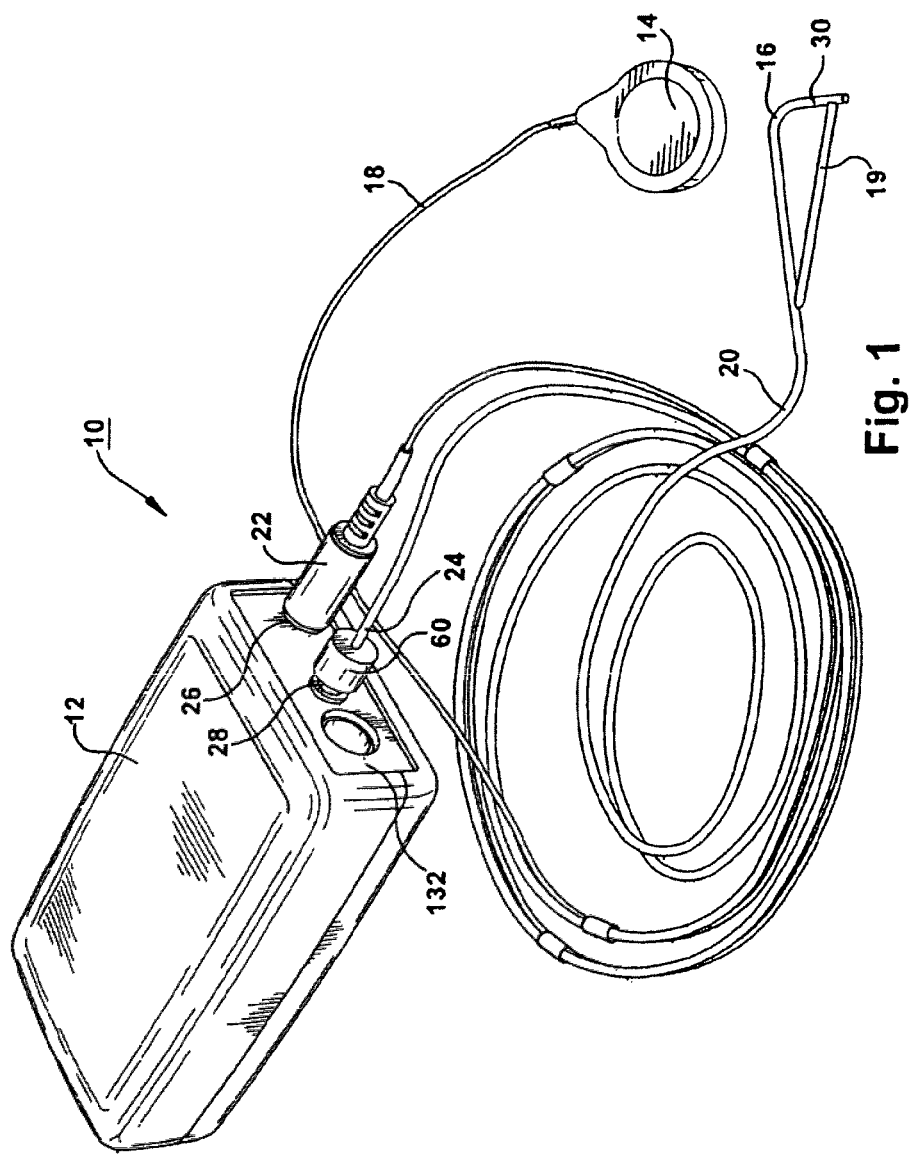

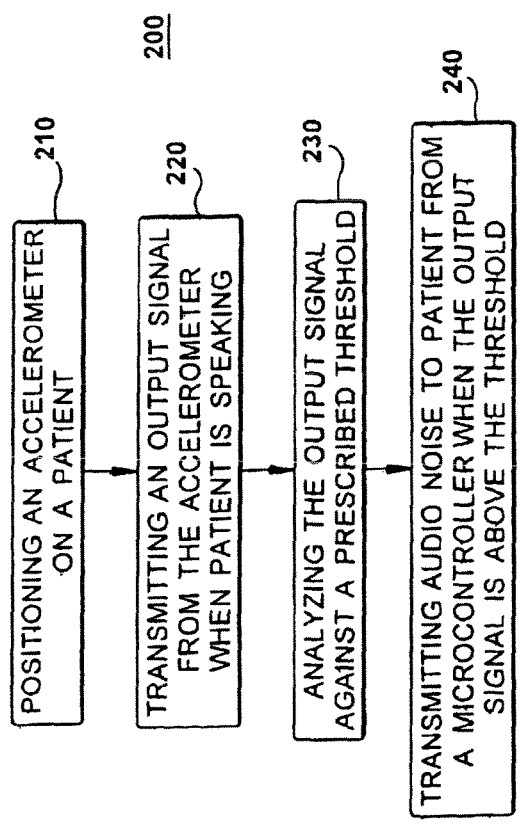

DEVICES THAT TRAIN VOICE PATTERNS AND METHODS THEREOF

This application is a continuation-in-part of U.S. patent application Ser. No. 14/266,289 filed on Apr. 30, 2014, which is a continuation of U.S. patent application Ser. No. 13/835,802 filed Mar. 15, 2013, which is a continuation-in-part of PCT/US2010/045568 filed Aug. 16, 2010, which claims the benefit of U.S. Provisional Application No. 61/234,401 filed Aug. 17, 2009, each of which is hereby incorporated by reference in its entirety.

U.S. application Ser. No. 13/835,802 is also a continuation-in-part of U.S. application Ser. No. 13/398,399 filed Feb. 16, 2012, which claims the benefit of U.S. Provisional Application No. 61/445,780 filed Feb. 23, 2011, and is a continuation-in-part of PCT/US2010/045568 filed Aug. 16, 2010, which claims the benefit of U.S. Provisional Application No. 61/234,401 filed Aug. 17, 2009, each of which is hereby incorporated by reference in its entirety.

U.S. application Ser. No. 13/835,802 is a further a continuation-in-part of PCT/US2012/026033 filed Feb. 22, 2012, which is a continuation of U.S. application Ser. No. 13/398,399 filed Feb. 16, 2012, which claims the benefit of U.S. Provisional Application No. 61/445,780 filed Feb. 23, 2011, and is a continuation-in-part of PCT/US2010/045568 filed Aug. 16, 2010, which claims the benefit of U.S. Provisional Application No. 61/234,401 filed Aug. 17, 2009, and which claims the benefit of U.S. Provisional Application No. 61/445,780 filed Feb. 23, 2011, each of which is hereby incorporated by reference in its entirety.

GOVERNMENT FUNDING

This invention was made with government support under National Institutes of Health ("NIH") Grant No. ROI DC009409. The United States government has certain rights in the invention.

FIELD

This technology relates to a device for training voice patterns, and more specifically, This technology comprises a voice enhancement device and method used to increase individuals' sound pressure level ("SPL") and change their speech rate. The voice enhancement device and method increase the individuals' SPL and changes their speech rate by eliciting the Lombard effect. The Lombard effect is an external cue for increasing voice loudness.

BACKGROUND

Individuals can suffer from various diseases that result in one or more voice impairments. Such voice impairments can include, but are not limited to, hypophonia (reduced loudness), monoloudness, monopitch, disordered rate and articulation, and a voice that is hoarse, breathy, harsh, and/or tremulous.

Parkinson's Disease is a progressive movement disorder in which there is a deficit in dopamine production in the basal ganglia. Parkinson's Disease is just one disease identified as being associated with one or more voice impairments. Parkinson's Disease may cause motor speech disorders such as hypokinetic dysartharias wherein intensity (loudness of the voice) is a problem. Further discussion relating to Parkinson's Disease and its connection with voice impairments is found in International Patent Application Serial Number PCT/US2010/045568 filed Aug. 16, 2010 entitled METHOD AND APPARATUS FOR INCREASING VOICE LOUDNESS, hereinafter referred to as "the 568 Application". The '568 Application is incorporated herein by reference in its entirety for all purposes.

SUMMARY

A voice enhancement device including an earpiece configured to be positioned in an ear canal of a user. A microcontroller is operatively coupled to the earpiece. The microcontroller is configured to selectively provide at least multitalker babble. An accelerometer is located within the earpiece and operatively coupled to the microcontroller. The accelerometer is configured to detect speech by the user and communicate with the microcontroller to provide the multitalker babble to the earpiece during the detected speech by the user.

A method of making a voice enhancement device includes providing an earpiece configured to be positioned in an ear canal of a user. A microcontroller is operatively to the earpiece, wherein the microcontroller is configured to selectively provide at least multitalker babble. An accelerometer located in the earpiece is operatively coupled to the microcontroller, wherein the accelerometer is configured to detect speech by the user and communicate with the microcontroller to provide the multitalker babble to the earpiece during the detected speech by the user.

A method for increasing vocal loudness in a patient includes positioning an earpiece comprising an accelerometer in an ear canal of the patient. A microcontroller operatively coupled to the earpiece is provided, wherein the microcontroller is configured to selectively provide at least multitalker babble to the earpiece, and further wherein the accelerometer is configured to detect speech by the patient and communicate with the microcontroller to provide the multitalker babble to the earpiece during the detected speech by the patient.

The present technology provides a number of advantages including providing a voice enhancement device that provides a source of multitalker babble to a user's ear through an earpiece during the user's speech, resulting in several positive and trained conditions in the patient, including increased sound pressure levels, normalized speech rate, improved respiratory support, and improved articulation. The earpiece advantageously incorporates an accelerometer located with the earpiece to detect the user's speech based on vocal fold vibrations that resonate near the user's ear canal. This provides a more compact, discreet device for providing the described voice enhancement benefits.

BRIEF DESCRIPTION OF THE DRAWINGS

The foregoing and other features and advantages of the present disclosure will become apparent to one skilled in the art to which the present disclosure relates upon consideration of the following description of the invention with reference to the accompanying drawings, wherein like reference numerals, unless otherwise described refer to like parts throughout the drawings and in which:

FIG. 1 is a voice enhancement device constructed in accordance with one embodiment of the present disclosure;

FIG. 11 is a flowchart summarizing a method for increasing voice loudness in a patient in accordance with one embodiment of the present disclosure;

DETAILED DESCRIPTION

Figure 2A:
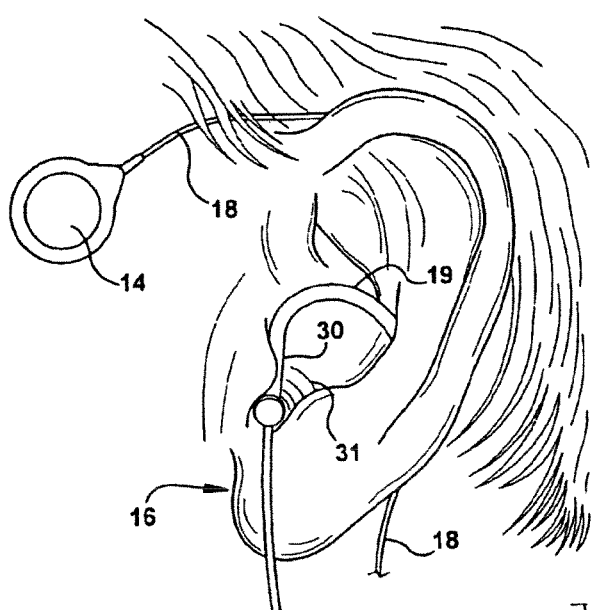
FIG. 2A is an earpiece positioned within an ear of a patient using the voice enhancement device and methods for treatment and the positioning of an activation device in accordance with one example embodiment of the present disclosure.

The present disclosure relates generally to a voice enhancement device, a method making a voice enhancement device, and a method for training voice patterns using the device. More specifically, the present disclosure comprises a voice enhancement device and method used to increase individuals' SPL and change their speech rate. The voice enhancement device and method increases the individuals' SPL and changes their speech rate by eliciting the Lombard effect. The Lombard effect is an external cue for increasing voice loudness. The present method and device use the Lombard effect to assist individuals experiencing problems with vocal intensity, articulation, and/or volume as a result of a physically degenerative condition such as Parkinson's Disease.

The Lombard effect produces an involuntary reaction in speakers to increase their voice loudness when speaking in noisy environments. In addition, the Lombard effect is known to not only influence the voice loudness in its speakers, but it can also alter the speaker's articulation quality, speech rate, and pitch. The present disclosure also provides a more compact, discreet training device that incorporates an accelerometer directly into an earpiece of the device to detect the user's speech.

Referring now to the figures, and in particular to FIG. 1, is a voice enhancement device 10 constructed in accordance with one embodiment of the present disclosure. The voice enhancement device 10 comprises a number of components and is designed to be used with patients diagnosed with physical ailments resulting in reduced vocal volume or intensity and experiencing problems with vocal loudness as a result of their Disease.

Parkinson's Disease, including idiopathic Parkinson's Disease is an example of one type of ailment treatable by the device 10; however, other diseases or speech disorders having similar ailments that can cause speech deficiencies, for example hypophonia, general articulation, low sound pressure level, high speech rates, reduced respiratory support, and poor vowel articulation are intended to be treated with the voice enhancement device 10 without departing from the spirit and scope of this disclosure.

The voice enhancement device 10 as shown in FIG. 1 comprises a number of electrical components that are both internal and external to a housing 12. Located externally from the housing 12 is an activation device or accelerometer 14 and earpiece 16 that are coupled via feeds 18, 20 having connectors 22, 24, respectively, to ports 26, 28 of the housing. In one example embodiment, the accelerometer 14 is an accelerometer manufactured by Knowles Acoustics of Itasca, Ill. under part number BU-27135-000. In another example embodiment, the activation device 14 is a sensor capable of transforming energy from one form to another such as a transducer. In yet another example embodiment, the activation device 14 comprises a piezoelectric, piezoresistive, or capacitive type accelerometer.

The accelerometer 14 acts as an input device to the enhancement device 10. The accelerometer 14 is relatively unaffected by noises in the environment. The accelerometer 14 was chosen, rather than a microphone, so that the enhancement device 10 would not be activated as a result of noise in the room or communication by a third person's speech. Stated another way, the activation device or accelerometer 14 provides an input signal to the voice enhancement device 10 that detects the initiation and duration of the patient's speech and is not activated by surrounding noise and/or non-patient noise. Thus, the accelerometer 14 is an example of means for detecting when the user speaks and is an example of means for detecting when the user stops speaking.

During treatment, the accelerometer 14 is placed on any body part suitable for the activation device 14 is worn on or attached to a portion of the patient's neck, such as on a skin surface adjacent one or both of the of thyroid lamina or in the sternal notch. In yet another example embodiment shown in FIG. 2A, the accelerometer 14 is worn on or attached to the surface of the patient's skin covering the temporal bone to receive bone conduction vibrations resulting from vocal fold vibrations transmitted through the wearer's bones to detect the onset of speech. In a further embodiment shown in FIG. 2D, the accelerometer 14 is located within the earpiece 16, which is configured to be inserted into the wearer's ear canal. In this embodiment, the accelerometer 14 senses vibrations from vocal fold vibrations which are transmitted through the bones of the wearer's skull and resonate near the wearer's ear canal.

Figure 16:
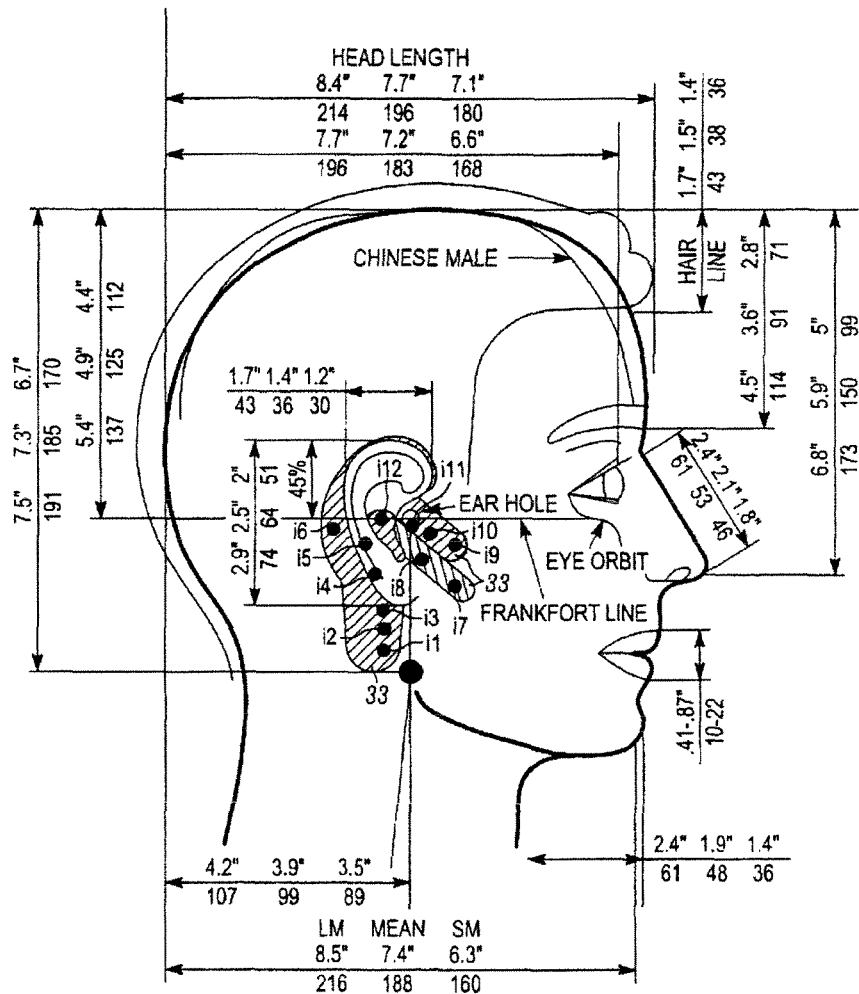
FIG. 16 illustrates various positions for locating an activation device of the voice enhancement device in accordance with one example embodiment of the present disclosure.

FIG. 16 illustrates various positions for locating an activation device 14 of the voice enhancement device 10 in accordance with one example embodiment of the present disclosure. In FIG. 16, the activation device 14 is positioned on or in contact with one of the soft tissue regions it-i12 about the patient's ear, the regions it-i12 were found to be highly sensitive to detecting speech vibrations.

The regions i1-i12 include the soft tissue area just under the mandible behind the ear lobe it-i6 and in front of the ear i7-i12. Each of the soft tissue regions i1-i12 identified for the positioning or contact of the activation device 14, advantageously allows for enhanced sensing of speech vibrations independent of the facial features of the patient.

Figure 2B:
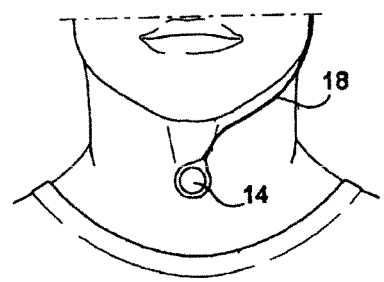
FIG. 2B illustrates another example embodiment for the positioning of an activation device for a voice enhancement device of the present disclosure.
Figure 2C:
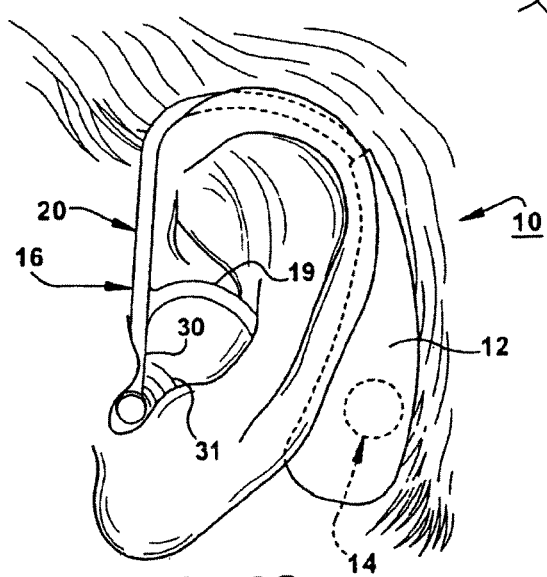
FIG. 2C illustrates an example embodiment of a voice enhancement device comprising a compact design where the entire device is positioned near the patient's ear.

While the activation device 14 could be positioned on any of the regions i1-i12 using an adhesive, in a preferred example embodiment, the activation device contacts the patient's skin from a fixture 33 extending from, or directly on the device 10, as illustrated in FIGS. 2A, 2C, and 16.

In an alternative example embodiment, the activation device 14 contacts one of the regions it-i12, as it attached and extending from a headset (such as a Bluetooth headset) coupled to the patient's ear. In such embodiment, the activation device 14 is not in continuous contact with the patient's skin.

Examples of body parts suitable for detection of speech initiation using the device 10, in addition to the temporal bones, neck, and ear canal as described above, include areas near the patient's mouth or lips. All of such body parts and positions are intended to be within the scope and spirit of the present disclosure.

Figure 2D:
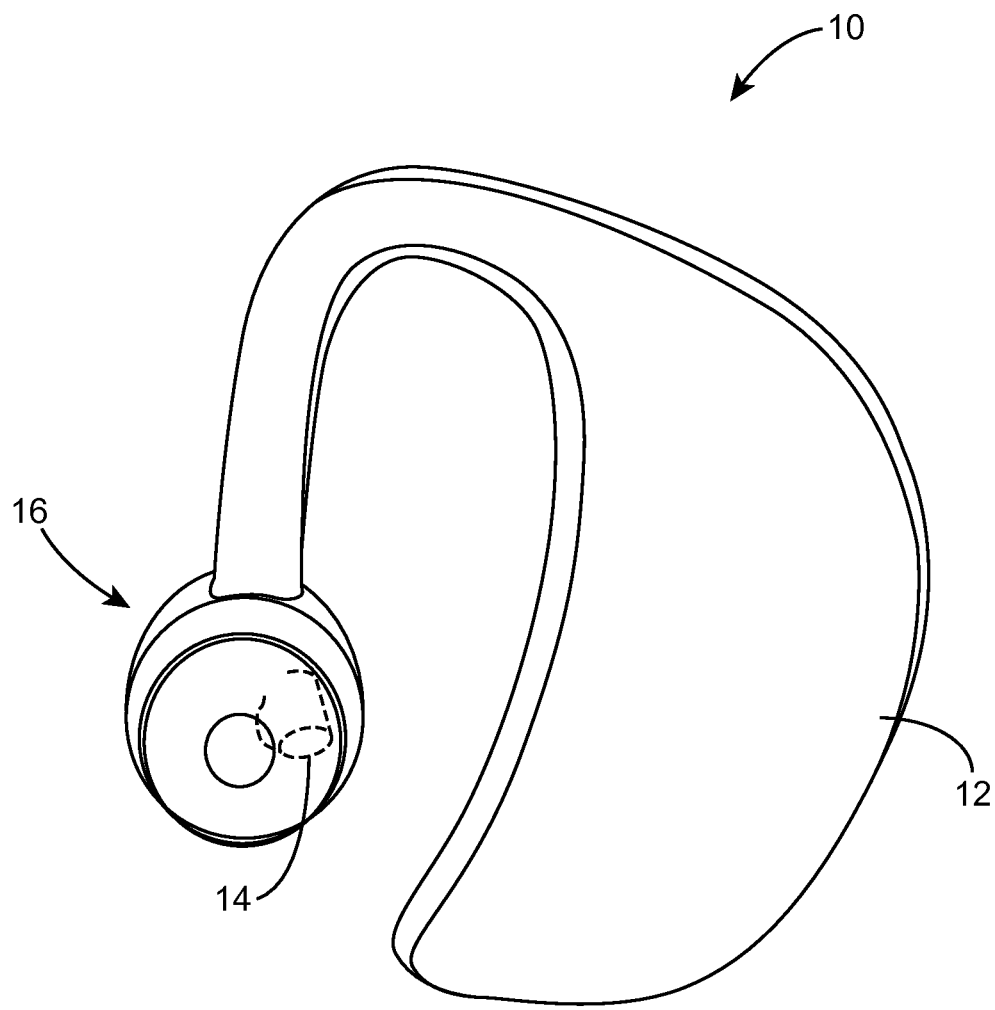
FIG. 2D illustrates an example embodiment of a voice enhancement device incorporating an accelerometer directly into the earpiece configured to positioned in the patient's ear canal.

In the example embodiment of FIG. 2A, the accelerometer 14 is attached in close proximity to the patient's ear. In both the embodiments of FIGS. 2A and 2B, the accelerometer 14 is attached to an epidermal surface using an adhesive. As shown in FIG. 2d, the accelerometer 14 is located within the earpiece 16 to be located in the wearer's ear canal.

The earpiece 16 acts as an output of the device 10, transmitting noise to the patient's ear during prescribed times during treatment. In one example embodiment, the prescribed time during a noise enabling condition starts when the patient initiates speech and continues while the patient talks and may continue for a prescribed duration when the patient ceases speech. The earpiece 16 is a monoaural device that, in the illustrated example embodiment is non-occlusive to the patient's ear. The non-occlusive earpiece 16 advantageously allows the patient to hear their own speech during use of the device 10. Such advantageous results would not be experienced at the same level with an occlusive earpiece, which would have a tendency to obstruct the patient's hearing. An occlusive earpiece would have the effect of making the patient's voice sound louder to themselves, causing them to talk more quietly. Use of a non-occlusive earpiece avoids this negative effect.

The earpiece 16 having a support 19 is fed to the ear of the patient through thin tubing or feed 20 and an open ear fitting 30 as best seen in FIG. 2A. A suitable example of earpiece 16 that includes a feed 20 and an open ear fitting 30 is a product manufactured by Phonak AG of Switzerland under the name Fit'nGo Kit; however other open ear fittings made by other manufacturers could also be used with the device 10. The open ear fitting 30 is typically fit into the patient's ear by an audiologist. Use of an open ear fitting 30 avoids a reduction in vocal intensity due to the occlusion effect, which can occur with a closed ear fitting.

In one example embodiment, the amplitude of the noise generated by the device 10 and transmitted to the output or earpiece 16 can be changed by a third party (e.g, a physician, speech-language pathologist, medical personnel etc.) treating the patient, but not by the user of the device. In the exemplary embodiment, the highest output level of the device 10 is less than 85 dBA, and ranges at levels below 80 dBA, which is adequate to elicit the Lombard Effect and would not be expected to cause damage to the hearing mechanism or hearing of the patient that is being treated. The device 10 with elements that limit the highest output thus comprises means to prevent hearing impairment.

Figure 3:
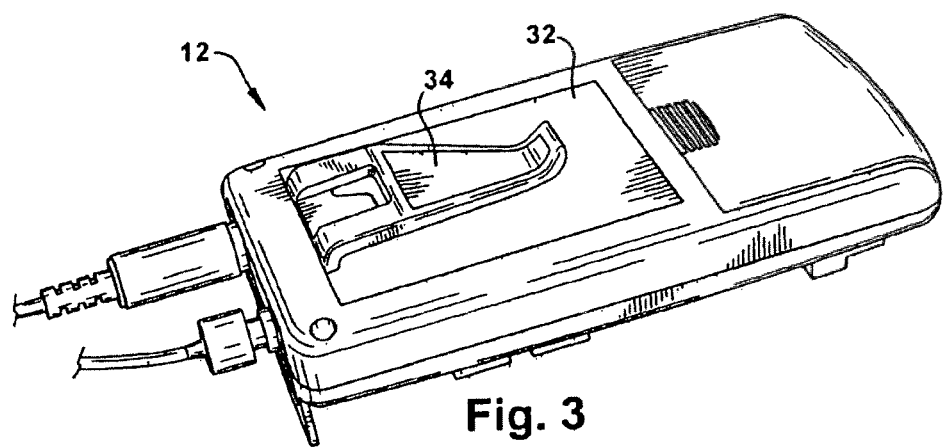
FIG. 3 is a rear cover of a housing for the voice enhancement device illustrated in FIG. 1.

Referring now to FIG. 3 is a rear perspective view of the housing 12 used to support a portion of the electronics of the voice enhancement device 10. The voice enhancement device 10 illustrated in the example embodiment of FIGS. 1 and 3 is a portable device, allowing unrestrained mobility of the patient since it is designed to attach to the patient's body. In particular, rear view of the housing 12 shown in FIG. 3 illustrates a rear cover 32 of the housing having a support clip 34 integrated into the cover for attaching to the patient's clothing during use. Alternatively, the support clip 34 is used to hold the device 10 by attaching it to the patient's waist through either a belt clip or a fanny pack (depending on the patient's preference). The feeds 18, 20 can be fed underneath the patient's clothing to reduce the visible impact, that is, making the device 10 more inconspicuous to the patient's environment.

In the illustrated example embodiment of FIG. 1, the device 10 weighs no more than 6 ounces. Illustrated in FIG. 2C is an example embodiment of a voice enhancement device 10 comprising a compact design where the entire device 10 is positioned near the patient's ear. In particular, the non-occlusive earpiece 16, housing 12, and activation device (e.g., accelerometer) 14 are in contact with the patient's ear. In the example embodiment of FIG. 2C, the activation device 14 is cased partially within the housing 12. The housing 12 in FIG. 2C contains all the electronics necessary, as further discussed below for processing signals from activation device 14 and producing noise 31 to the earpiece 16. The housing 12 also contains a power source such one or more batteries for supplying power to the device 10.

During treatment, the patient may wear the voice enhancement device 10 for several hours a day, increasing with treatment up to eight (8) hours per day. The treatment and design of the device 10 is such that it is highly mobile for the patient, allowing treatment to take place during daily living activities.

The device 10 is designed in such a way to externally cue the patient, for example, via the Lombard effect upon initiation of the patient's speech, resulting in several positive and trained conditions in the patient, including increased sound pressure levels, normalized speech rate, improved respiratory support, and improved articulation. In one embodiment, the device 10 during treatment generates noise 31 that is projected from the earpiece 16 into the patient's ear upon the initiation of the patient's speech. In yet another example embodiment, the noise 31 is communicative unintelligible noise, simulating unintelligible conversations between individuals, which is sent to the earpiece 16 worn in one of the patient's ears while he/she is talking Simulating unintelligible conversations is also referred to as multitalker babble noise. In one embodiment, the communicative noise 31 is generated from a product called Multitalker (20 Talkers) (MT) digital audio manufactured by AUDiTEC of St. Louis, Mo. In yet another example embodiment, the noise 31 is white noise and/or random noise.

The presence of communicated noise 31 received by the earpiece 16 is an external cue to the patient to talk louder, naturally eliciting louder and clearer speech through the Lombard Effect. The Lombard Effect provoked by the use of the device 10 causes the patient to naturally and automatically speak louder under conditions of background noise generated by the device. The device 10 is believed to be most effective when the noise transmitted to the patient's earpiece 16 is more communicative in nature. However, random noise could also be transmitted to the patient's earpiece 16 without departing from the scope and spirit of this disclosure. Individuals that suffer from hypophonia, which is found in some forms of Parkinson's Disease, can use the device 10 for treatment by wearing the device in natural communication contexts, achieving a louder, clearer, and more intelligible voice, without needing to self-cue.

Figure 4:
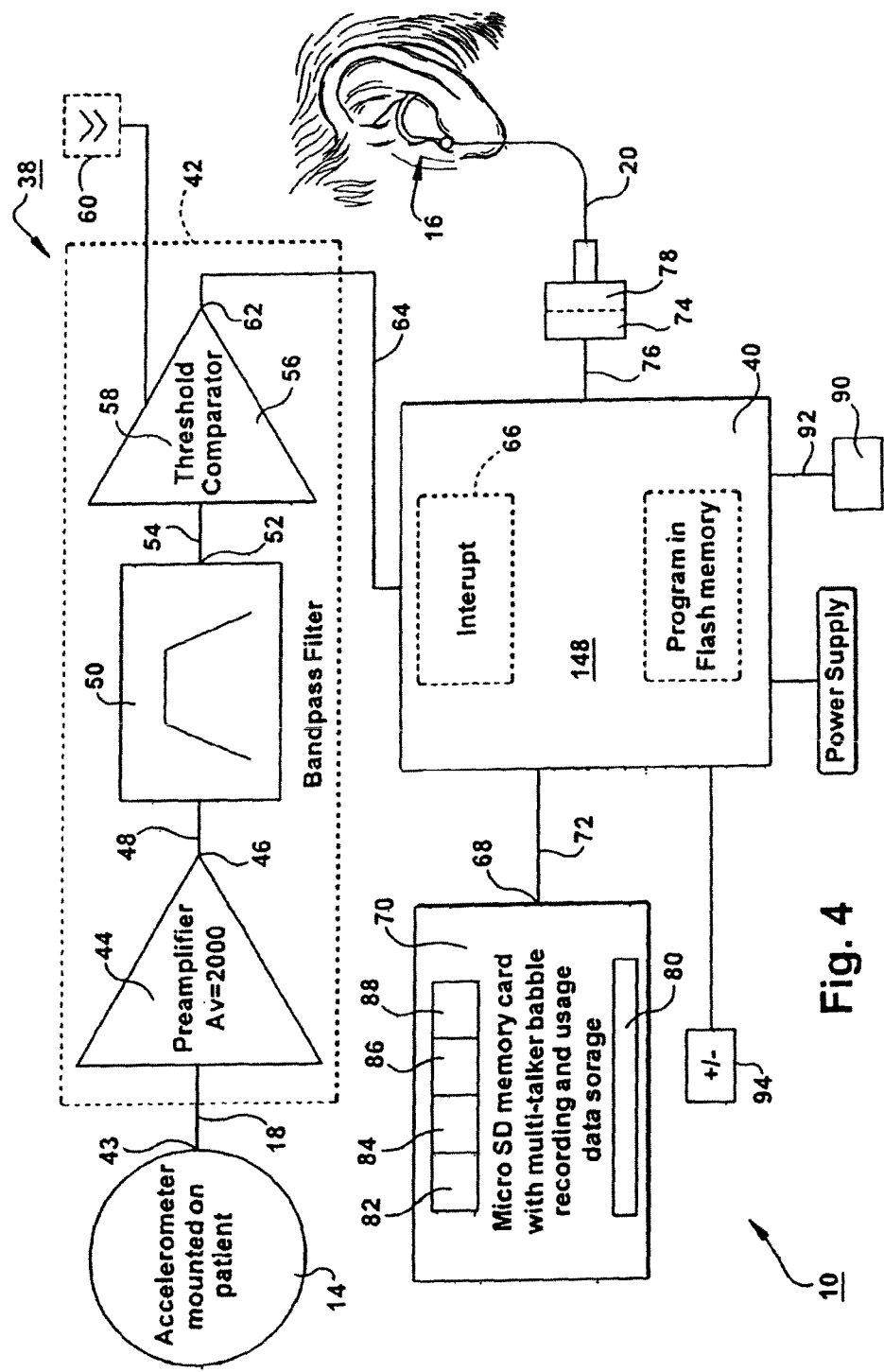
FIG. 4 is a block diagram illustrating a control arrangement of a voice enhancement device constructed in accordance with one embodiment of the present disclosure.

Illustrated in FIG. 4 is a block diagram depicting a control arrangement 38 forming the voice enhancement device 10 in accordance with one example embodiment of the present disclosure. The control arrangement 38 in block diagram of FIG. 4 illustrates generally the components of the device 10, further shown in detail in FIGS. 8-10 and how the electrical components are interconnected. Centrally located within diagram is a central processing unit ("CPU") or microcontroller 40. In one embodiment, the microcontroller 40 is a 16 Bit 120 K microprocessor. An example of a suitable microcontroller 40 is an MSP430F26 1 8TPN manufactured by Texas Instruments. As will be more fully discussed below, the device 10 as depicted in FIG. 4 is an example of means for providing noise that induces the Lombard effect to induce the user to speak louder, to one or more of the user's ears when the user speaks, and to terminate said noise when the user stops speaking.

Figure 5:
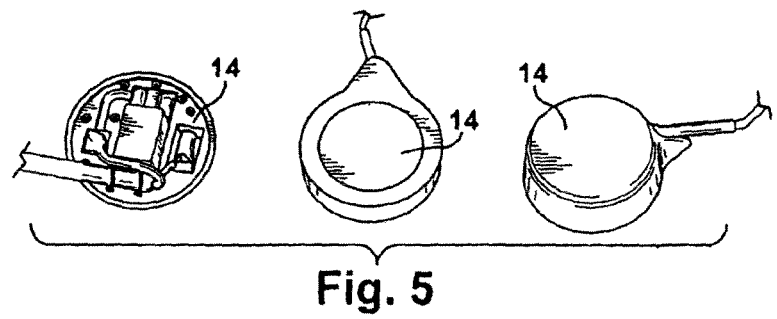
FIG. 5 are images of an accelerometer used in connection with one embodiment of the voice enhancement device.

The accelerometer 14 during use in one example embodiment is mounted on the patient's neck and is connected to electrical components 42 that are coupled to the microprocessor 40 using feed 18 (see FIGS. 1 and 5). In one example embodiment, the feed 18 is a thin, flexible cable and a 3.5 mm mini-phone audio connector 22 (see FIG. 1).

Referring again to FIG. 4, the connector 22 applies an output signal 43 upon speech by the patient generating movement detected by the accelerometer 14 to a preamplifier 44 with a gain of 2000. In one example embodiment, the accelerometer 14 activates the device 10 by sensing vibrations solely from the patient's vocal folds. An amplified signal 46 is transmitted through lead 48 that couples the preamplifier 44 to a bandpass filter 50. The band-pass filter 50 limits the frequency content of the signal 46 to form a filtered signal 52. In the illustrated example embodiment, the filtered signal 52 is limited by the band-pass filter 50 to a frequency content of approximately 100 HZ to 400 HZ.

The filtered signal 52 is transmitted via lead 54 that couples the band-pass filter 50 to a comparator 56. The filtered signal 52 is then compared by the comparator 56 to a reference level 58 that is set by an adjustment 60 located on the housing 12. Every time the amplitude of the filtered signal 52 exceeds the reference level 58, the comparator 56 changes state, from low to high in an output signal 62. The output signal 62 is transferred to the microcontroller 40 via lead 64. In one example embodiment, the output signal 62 switches between 3.3 volts DC to 0 volts DC when changing from high to low state.

When the filtered signal 52 value drops back below the reference level 58, the comparator 56 changes state from high to low. This produces a stream of pulses in the output signal 62 that are applied to an interrupt 66 located within the microcontroller 40. As the state in the filtered signal 52 changes from high to low or vice versa, the noise transmitted from the device 10 into the earpiece 16 of the patient is enabled and disabled as the change in state occurs. The adjustment 60 that changes the reference level 58 allows medical personnel (such as physicians, nurses, speech-language pathologists etc.) treating the patient to manually optimize the sensitivity of the voice enhancement device 10 to the needs of each individual patient. Stated another way, the adjustment 60 allows the threshold for enabling and disabling the noise 31 received by the patient through the earpiece 16 to be adjusted based on the output signal 43 transmitted by the accelerometer 14.

The interrupt 66 of the microcontroller 40 uses a subroutine to analyze the pulses in the output signal 62 from the comparator 56 to determine when the patient begins speaking. Once it is determined that the patient is speaking, the microcontroller 40 begins reading the communicative noise 31 or audio 68, such as the product Multitalker (20 Talkers) (MT) digital audio manufactured by AUDiTEC of St. Louis, Mo. from a micro memory card 70 that is coupled via lead 72 to the microcontroller. The microcontroller 40 then begins playing the communicative noise, random noise 31, or audio 68 through an amplifier 74 and a speaker 78 coupled to the microcontroller through lead 76 and feed 20 of the earpiece 16.

In the illustrated exemplary embodiment, the amplifier 74 is a Class D amplifier and is combined with the speaker 78, using a digital to analog converter located within the microcontroller 40. The speaker 78 is connected to the patient's ear with thin clear plastic tubing of the earpiece 16. One suitable example of the earpiece 16 and speaker 78 is a product called Fit'nGo Kit open ear fitting manufactured by Phonak AG of Switzerland.

In one example embodiment, the microcontroller 40 is programmed 140 (see FIG. 9) via software such that once the patient stops speaking for approximately 0.5 seconds, the microcontroller 40 stops playing the audio 68 or communicative noise 31. In another example embodiment, the software is programmed such that the audio or communicative noise 31 continues to occur for a range of approximately 500-750 milliseconds. This reduces breaks in audio 68 or communicative noise 31, which could be irritating to the patient during voiceless sound periods.

When the patient starts talking again, the microcontroller 40 continues playing the audio 68 or communicative noise 31 from where it stopped previously, although the microcontroller may also play the audio 68 or communicative noise 31 from a random location in the recording. In yet another example embodiment, the micro memory card 70 contains about 12 minutes and 30 seconds of communicative noise 31 or audio 68 data on a data file 80 located within the memory card, although the micro memory card 70 may contain other longer or shorter amounts of communicative noise 31 or audio 68 data on a data file 80 located within the memory card. Once the entire audio data file 80 is played, the entire data file is started over at its beginning. This ensures that there is no obvious repetition of the audio generating the communicative noise 31 or audio 68.

The micro memory card 70 is also used to store data 82 about the usage of the voice enhancement device 10. When the audio or communicative noise 68 begins playing, a data record 84 is written to the memory card 70. Also when the audio 68 stops, another data record 86 is written to the memory card. The memory card 70 further contains a patient information record 88 that includes the patient number, as well as the date and time that the device 10 was initialized. Each patient information record 88 further contains audio 68 ON/OFF occurrences, elapsed time in days, hours, minutes, seconds and hundredths of seconds since the device 10 was initialized. Additional patient information record 88 includes the intensity of the speech vibrations detected by the accelerometer 14, as well as the relative sound output 31, 68 by the microprocessor 40.

The voice enhancement device 10 is designed to be connected to a computer 90 using a serial interface 92. However, other interfaces 92, including USB, remote, and wireless connections for communicating the computer 90 and the device 10 are also viable forms of communication covered by the spirit and scope of this disclosure. The usage data 82-88 can then be downloaded from the device's memory card 70 via the interface 92 to the computer 90. In the exemplary embodiment, the usage data 82-88 is downloaded to the computer 90 using a program called PKTalker that is written in LabVIEW. In an alternative example embodiment, an application specific program in the form of computer readable media is created for reading the usage data 82-88 by a computer 90.

Figure 7:
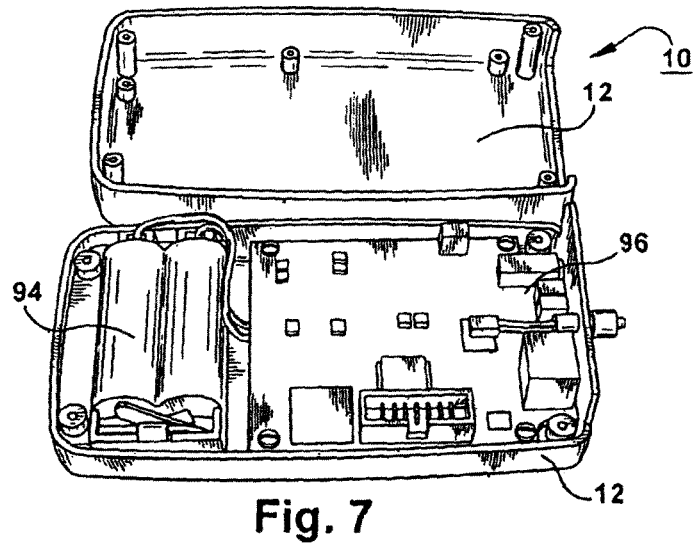
FIG. 7 is a portion of the voice enhancement device illustrating the positioning of the printed circuit hoard of FIG. 6 within a housing.

The device 10 receives its power from a power supply 94. In the illustrated example embodiment, the source of the power supply 94 is two AA alkaline batteries that depending on usage, will provide power to the device to operate for approximately 7-10 days on one set of batteries. As best seen in FIG. 7, the batteries that act as the power supply 94 are located within the housing 12. In an alternative example embodiment (for example FIG. 2C), the power supply 94 supporting the device 10 is smaller and uses for example a rechargeable battery that is charged via a USB connection to the device, although the battery may be charged using other types of connections and charging devices.

Figure 6:
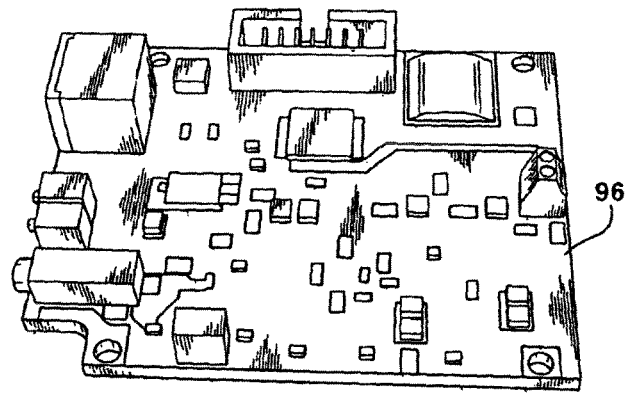
FIG. 6 is a printed circuit board of the voice enhancement device.

Illustrated in FIG. 6 is a printed circuit board ("PCB") 96 used to support a portion of the electrical components 42 circuitry 100, microcontroller 40, and micro memory card 70 used within the device 10. The PCB 96 is located within the housing 12 as best seen in FIG. 7. The PCB 96 used by the device 10 is a four (4) layer PCB and constructed using surface mount components.

In an alternative exemplary embodiment, the device 10 further comprises hardware to allow for external communication to a remote computer source. In one example embodiment, the device 10 includes a universal serial bus ("USB") or wireless connection, allowing communications with a remote computer for retrieving data and programming the data card 70.

In another alternative example embodiment, the device 10 is small enough for mounting to allow the accelerometer or transducer 14 to attach with a short connection to the patient's ear. One example embodiment is constructed such that the entire device 10 is small enough to be configured for positioning behind the patient's ear with the accelerometer 14.

In yet another alternative example embodiment, the device 10 uses an open wireless protocol, such as Bluetooth to deliver the audio to the patient's ear with a wireless connection to the accelerometer 14. In the alternative example embodiment, the device 10 is constructed to work with a Bluetooth headset, using processing capabilities of the microphone signal to determine when the patient is talking instead of the accelerometer 14.

The accelerometer 14 is coupled to the device 10 via the connector 22, which is shielded cable. In the illustrated example embodiment showing an electronic circuitry 100 of the device 10 in FIG. 8, the connector 22 is a 3.5 mm mini-phone audio jack. Two ferrite beads, Li and L2, are connected between an input lead 102 and reference lead 104 from the accelerometer 14 to an input 106 of the preamplifier 44 and an internal ground reference 108 of the device 10.

The ferrite beads, L1 and L2 attenuate radio frequency noise picked up by the accelerometer 14 and connector 22. The ferrite beads L1 and L2 also attenuate radio frequency noise created by the device's microcontroller 40 to reduce the device's 10 radio frequency emissions. In the illustrated example embodiment, the size of the ferrite beads Li and L2 have a 330 ohm impedance at 100 Mhz.

Figure 8:
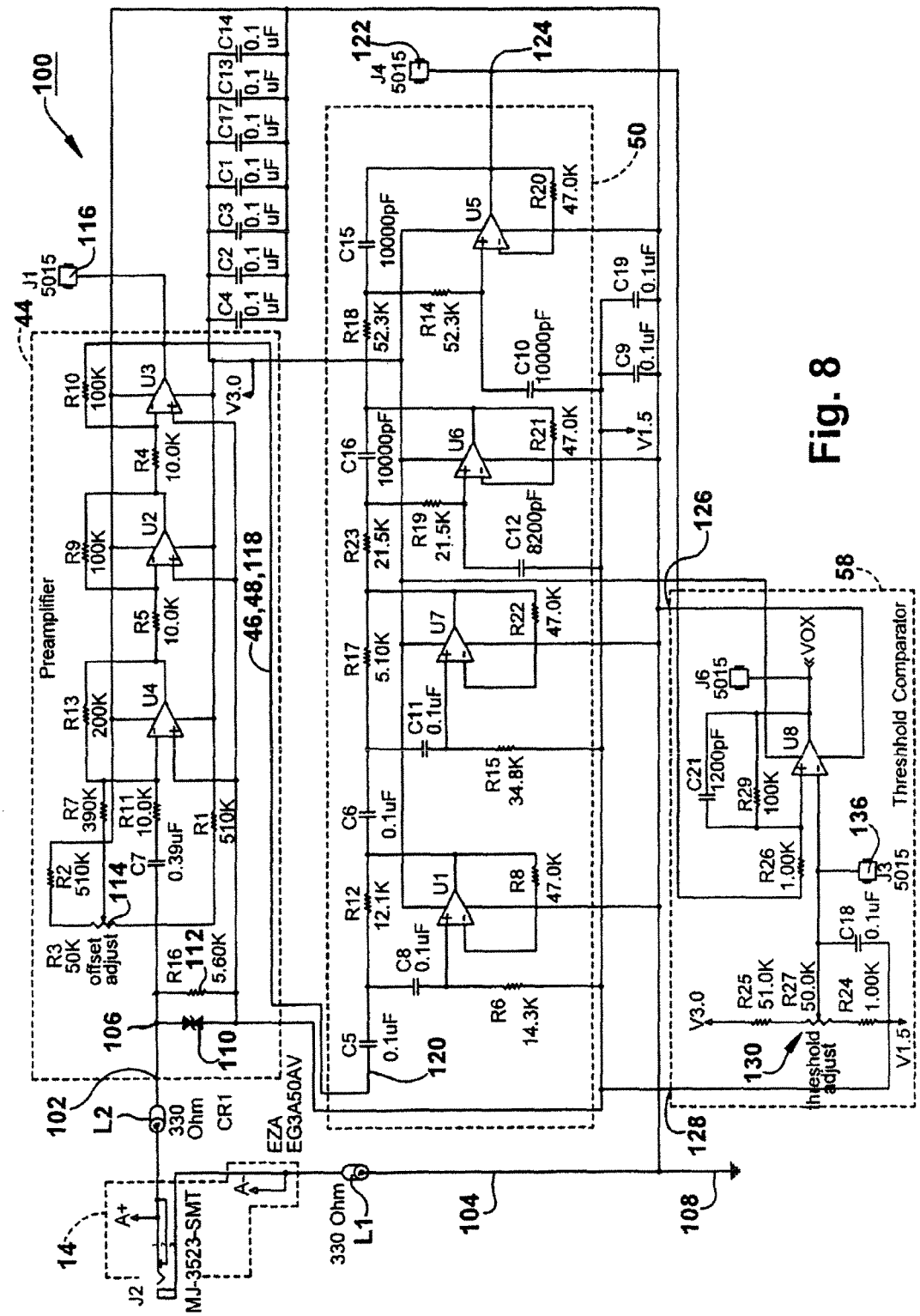
FIGS. 8, 9A-9C, and 10A-10B are electrical schematics forming the control arrangement of the voice enhancement device constructed in accordance with one example embodiment of the present disclosure.

In FIG. 8, an electrostatic discharge suppressor ("ESD") 110 also identified in the electrical schematic as CR1 protects the preamplifier 44 input 106 from static discharges. A resistor 112 also identified in the electrical schematic as R16 is an appropriate load resistor for the accelerometer. In the illustrated embodiment, the resistor 112 is a 5.6K Ohm 0.1 W rated resistor. The dashed box representing the preamplifier 44 contains three (3) operational amplifiers ("OP-AMPS") that combine to produce a voltage gain of 2000×. A variable potentiometer 114 also identified in the electrical schematic as R3 is used to adjust the DC balance of the preamplifier 44. A test point 116 also identified in the electrical schematic as J1 is used to analyze the preamplifier 44 output and to adjust the DC level to 1.5 volts with no signal present.

The amplified signal 46 is transmitted by an output 118 from the preamplifier 44 along lead 48 to an input 120 of the band-pass filter 50. In the illustrated example embodiment, the band-pass filter 50 is a fourth (4th) order band-pass filter that is centered at approximately 200 HZ. A test point 120 also identified in the electrical schematic as J4 is used to observe an output 124 of the band-pass filter 50.

The output 124 of the band-pass filter 50 is connected to one input 126 of the comparator 56. Another input 128 of the comparator 56 is connected to the adjustable voltage reference 130 formed by R25, R27, R24 and C18. R27 is a potentiometer connected to a variable adjustment 60 that is accessible from the front panel 132 (see FIG. 1). The variable adjustment 60 in combination with potentiometer R27 is used to adjust the amplitude at which the device 10 detects that the patient is speaking through the vibration, movement of muscle, facial tissue, etc., generated during speech. This allows the sensitivity of the device 10 to be set for a given patient. A test point 136 also identified in the electrical schematic as J3 is used to monitor the reference level during initial testing and adjustment. An additional test point, identified as reference character J6 in the electrical schematic is used to monitor the comparator output 62 to the microcontroller interrupt 66.

Figure 9A:
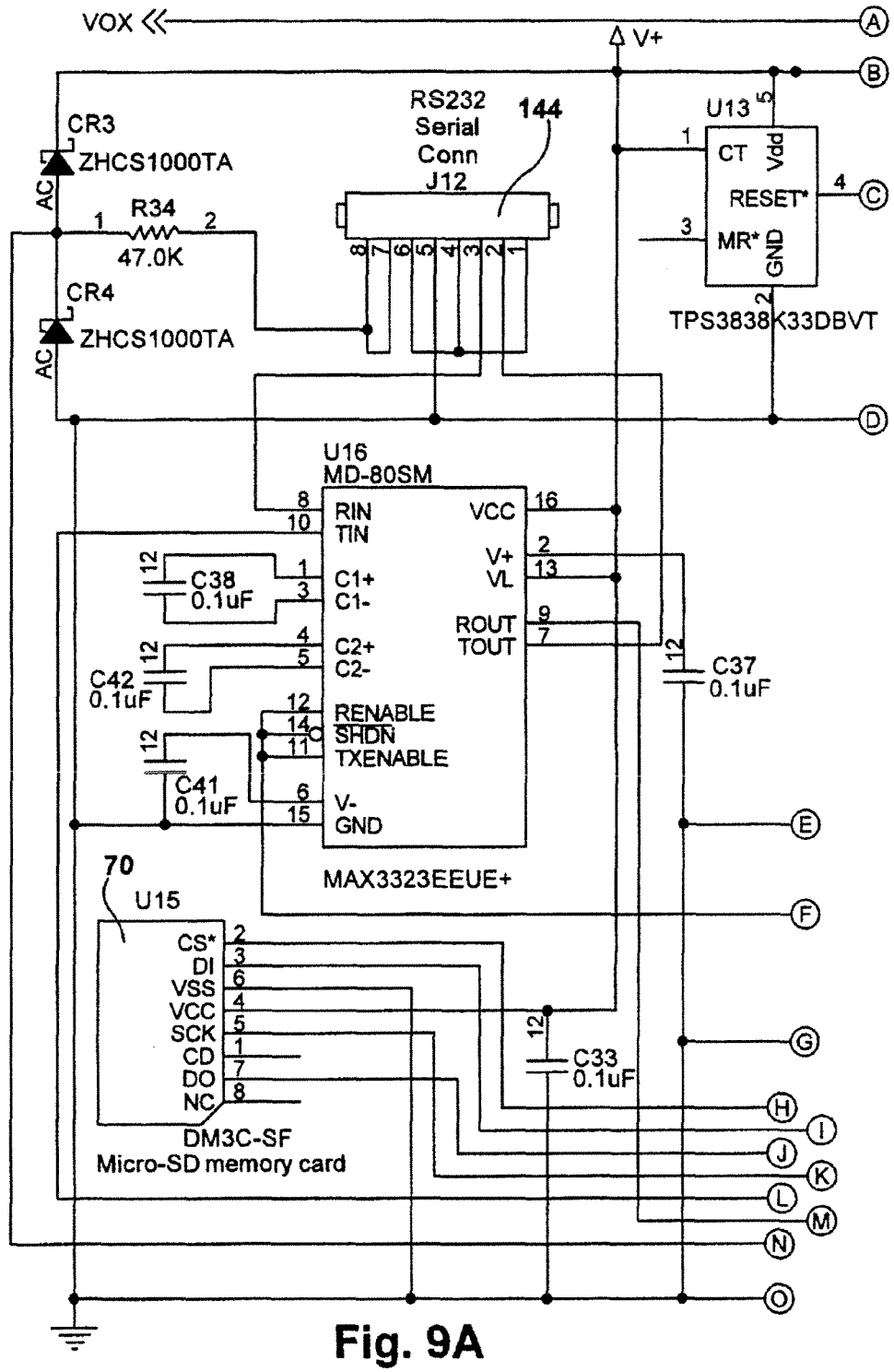
Figure 9B:
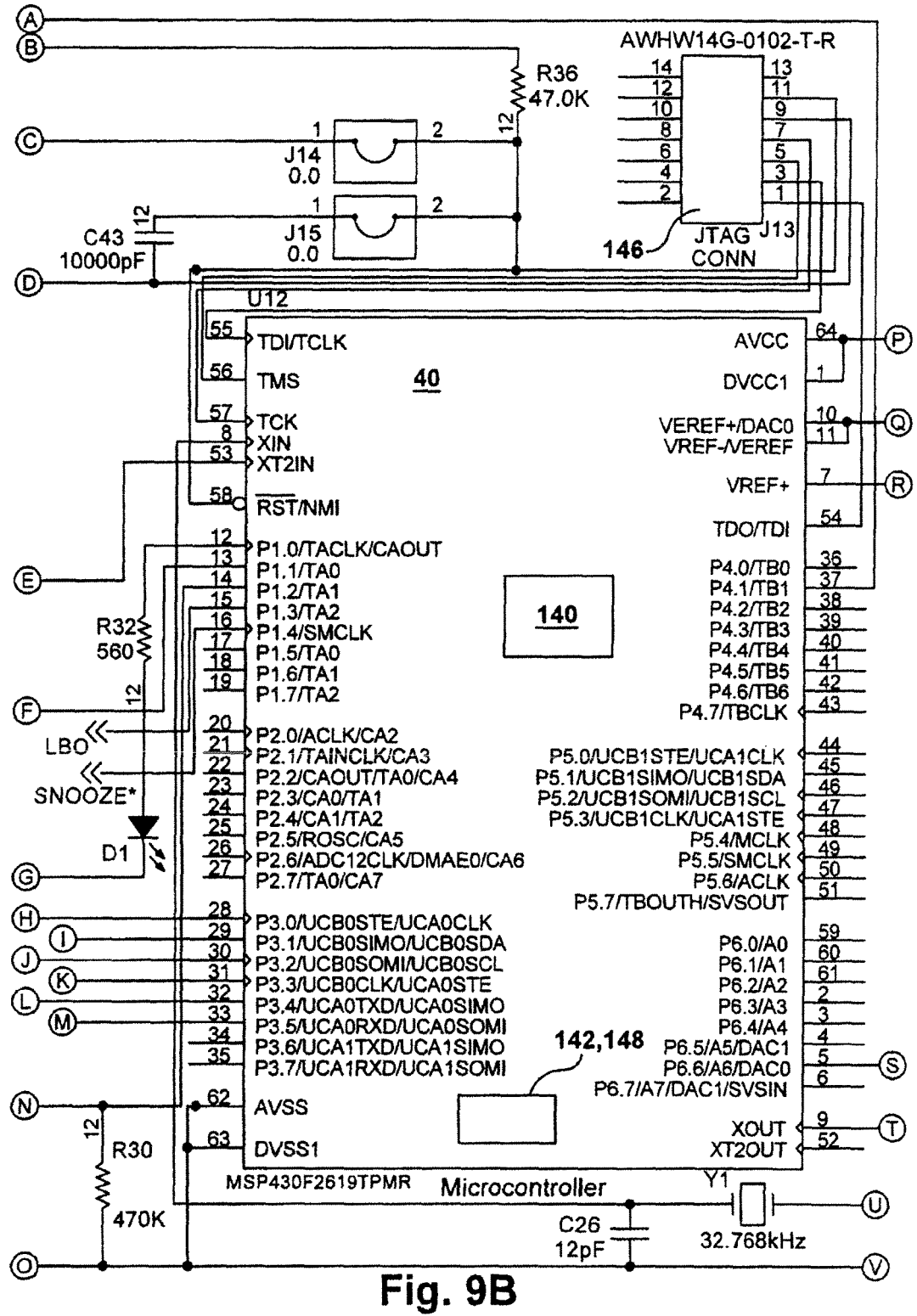
Figure 9C:
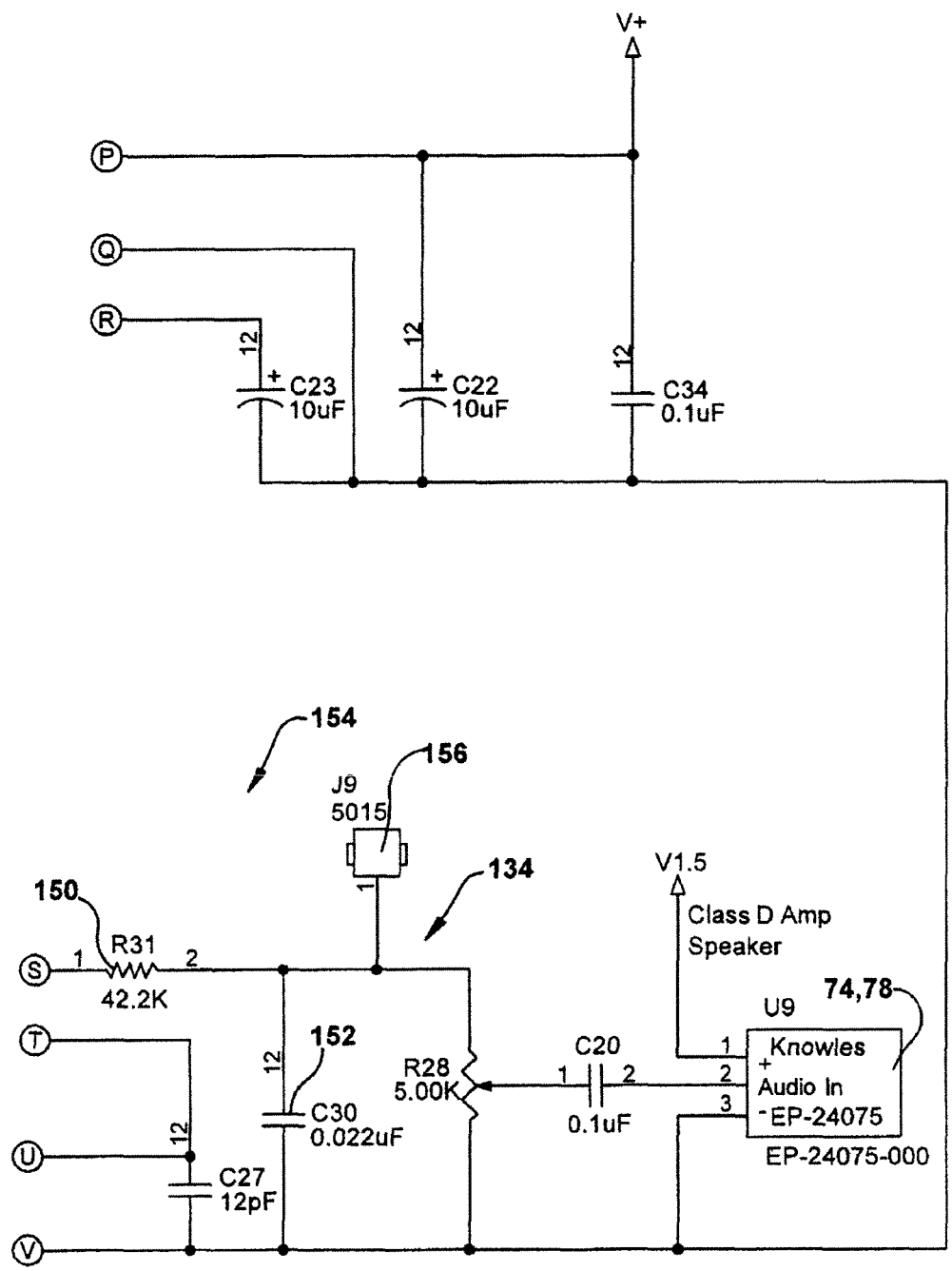

FIG. 9 shows that the output of the level comparator 58 (VOX) is connected to pin 37 (P4.1/TB 1) of the TMS430F2618 microcontroller 40 also identified in the electrical schematic as U12. Pin 37 is configured in software to function as an interrupt. The device 10 includes a program 140 internal to the microcontroller 40 that uses this interrupt to trigger the playback of the audio 68 to the patient. The audio data 82-88 is stored in memory card 70 also identified in the electrical schematic as 1J15. The memory card 70 is connected to the microcontroller 40 using an SPI serial interface connection to UC 130 (serial interface). The device program 140 also stores patient usage data 88 in flash memory 142 (see FIG. 9) every time the audio 68 is played.

Connector 144 also identified in the electrical schematic of FIG. 9 as J12 is an RS232 serial interface IC U16 used to connect the device 10 to a serial interface of a computer 90 so that the usage data 82-88 can be read from the flash memory 142 and the flash memory can be cleared of the usage data. The clearing of data in flash memory via software is understood by one skilled in the art. In the illustrated embodiment, the usage data 82-88 stored in the flash memory 142 is cleared using custom software written in LabView. The software code or operating program 148 used to operate the device 10 and is downloaded into the microcontroller 40 using conventional interfaces appreciated by one skilled in the art. A JTAG connector 146 also identified in the electrical schematic as J13 is used during testing and loading of the device's 10 operating program 148 into the microcontroller's flash memory 142.

The amplifier 74 and speaker 78 module also identified in the electrical schematic as U9 is used to deliver the audio 68 to the patient. The amplifier 74 and speaker 78 are connected to the microcontroller 40 digital-to-analog output. Pin 5 is also identified in the electrical schematic FIG. 9 as (DACO). In the exemplary illustrated embodiment, the audio 68 is delivered to the patient through a 0.05 inch ID 0.09 inch OD piece of TYGON® tubing 20 (see FIG. 1) manufactured by Saint-Gobain Performance Plastics Corporation of Aurora, Ohio. In the illustrated example embodiment, the audio data 80 is output from the microcontroller 40 at a sample rate of 8 kHZ.

Resistor 150 and capacitor 152, also identified in the electrical schematic as R31 and C30, respectively form a low pass filter 154 used to attenuate converter artifact. In the illustrated example embodiment, the low pass filter 154 attenuates converter artifact that is over approximately 5 kHZ. The externally accessible potentiometer 134 also identified in the electrical schematic as R28 is used to adjust the amplitude of the output audio 68 signal. A test point 156 also identified in the electrical schematic as J9 is used to measure the audio output signal 68 during device testing.

Figure 10A:
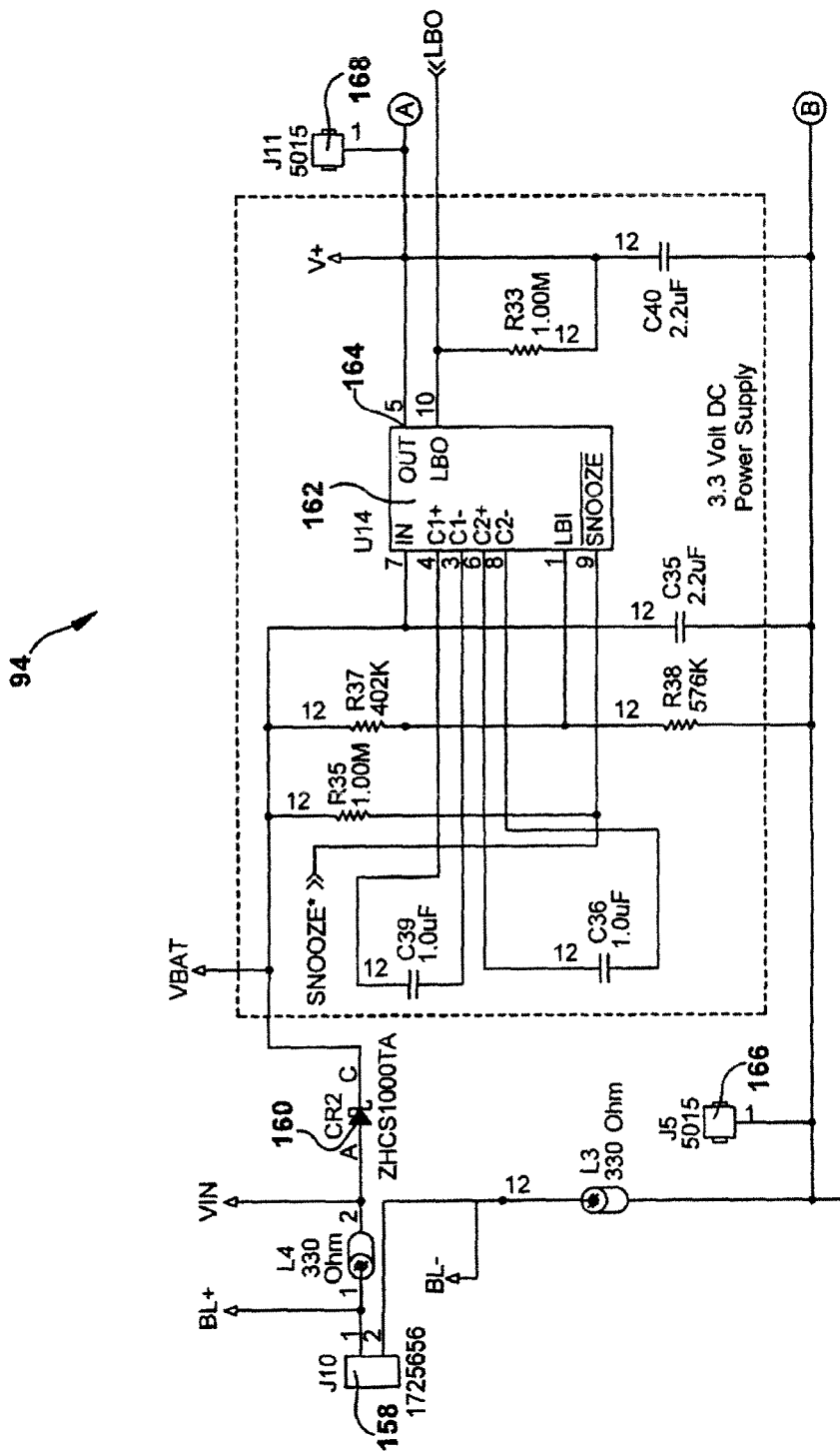
Figure 10B:
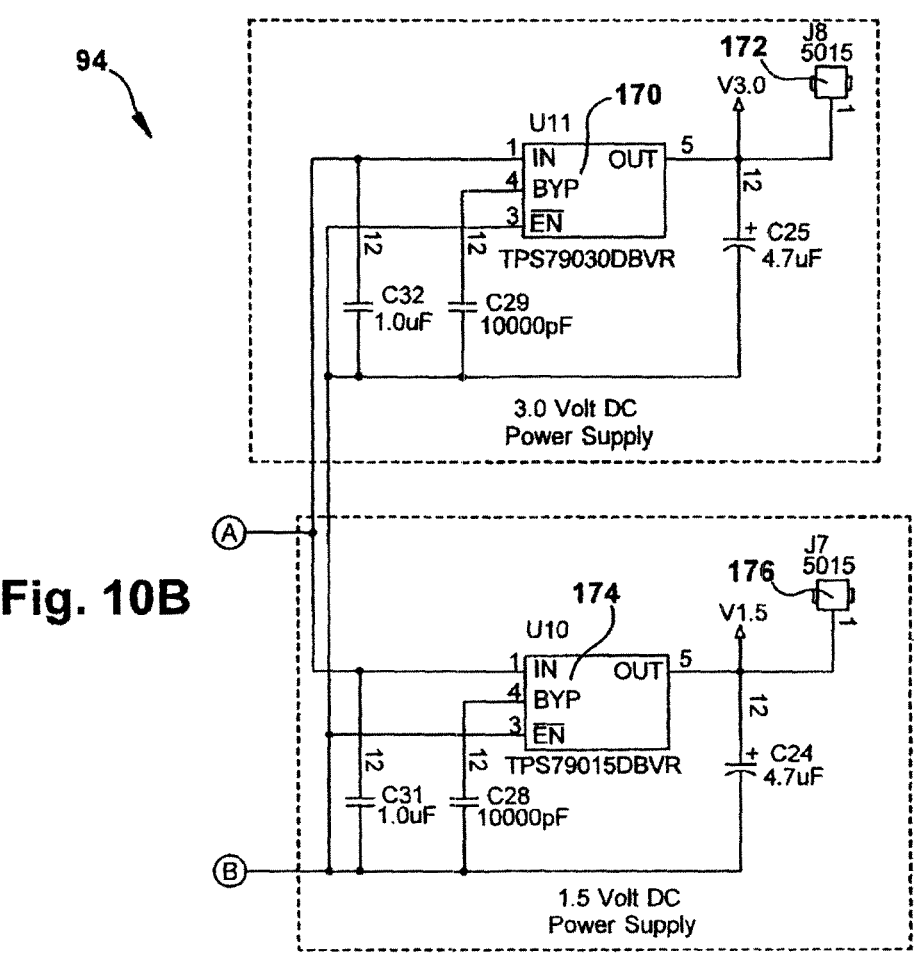

FIGS. 10A and 10B illustrate the schematics for the device power supplies 94. A screw terminal connector 158 also identified in the electrical schematic as J10 is coupled to the two battery power source. In the illustrated embodiment, two (2) AA batteries are used to power the device 10. In an alternative example embodiment, the power supplies 94 comprise a single or multiple rechargeable battery or batteries. L3 and L4 are ferrite heads used to attenuate RF interference. In the illustrated embodiment, the L3 and L4 ferrite beads have a 330 ohm impedance at 100 Mhz.

A Schottky diode 160 also identified in the electrical schematic as CR2 is used to protect the power supply 94 from backward connected batteries. A switched capacitor power supply regulator IC 162 also identified in the electrical schematic as L1 14 produces a main DC power supply 164 for the device 10. In the illustrated embodiment, the main DC power supply 164 provides 3.3 volts DC of power to the digital circuitry of the device 10. A test point 166 also identified in the electrical schematic as J5 connects a reference for measurements made during device setup and testing. A test point 168 also identified in the electrical schematic as J11 is used to check the main DC power 164.

A low dropout linear regulator 170 also identified in the electrical schematic as U11 provides regulated DC power for the analog and audio circuitry in the device 10. In the illustrated example embodiment, the linear regulator 170 provides 3.0V DC power to the analog and audio circuitry in the device 10. A test point 172 also identified in the electrical schematic as J8 is used to check the 3.0V DC supply. A low dropout linear regulator 174 also identified in the electrical schematic as U10 is used to provide 1.5 volt DC power for the device 10. The regulator 174 is used to power the amplifier 74 and speaker 78 as well as for a pseudo reference for the OP-AMPS in the preamplifier 44 and filter 50. A test point 176 also identified in the electrical schematic as J7 is used to check the 1.5V DC supply.

Illustrated in FIG. 11 is a flowchart summarizing a method 200 for increasing voice loudness in a patient in accordance with one embodiment of the present disclosure. At 210, the method 200 comprises positioning an accelerometer on a patient. At 220, the method 200 comprises transmitting an output signal from the accelerometer when the patient is speaking. At 230, the method 200 comprises analyzing the output signal against a prescribed threshold. At 240, the method 200 comprises transmitting audio noise to the patient from a microcontroller when the output signal is above the threshold.

An additional benefit of the device 10 is that the patient will be trained to use a louder voice even when not wearing the device over the course of the treatment period, leading to an extended therapeutic effect. For example, patients after using the device 10 for an extended period of time will produce louder and clearer speech, increasing a number of decibels (dBA) in SPL than experienced at the start of treatment without the device on. This therapeutic effect will beneficially grow over a treatment period using the device 10 on and off the patient, allowing the patient to maintain louder and clearer speech between longer treatment periods.

In one example embodiment, the device 10 is additionally used to measure a patient's SPL via the accelerometer 14, which provides feedback communications to the microcontroller 40. Alternatively or in combination with the accelerometer 14, a microphone 315 is coupled to the microcontroller 40 and used to provide SPL data relating to the patient during use of the device 10. The collection of the patient's SPL measurements occur with the device 10 on the patient, with or without the activation of the audio 68 or communicative noise 31.

In another example embodiment, the device 10 includes two or more settings that alter the levels of the audio 68 or communicative noise 31. For example, a first setting is used for normal or at home conditions. A second setting is used when increased audio 68 or communicative noise 31 is required, for example at a basketball game or large outdoor activity. Higher background noises in setting 2 can overcome the environmental competing effects of using setting one in louder environments. The settings can be adjusted by the patient manually, or alternatively, the microphone 315 can detect environmental conditions and the controller 40 can adjust the setting levels automatically.

Testing Results and Training Using the Voice Enhancement Device 10

Figure 12:
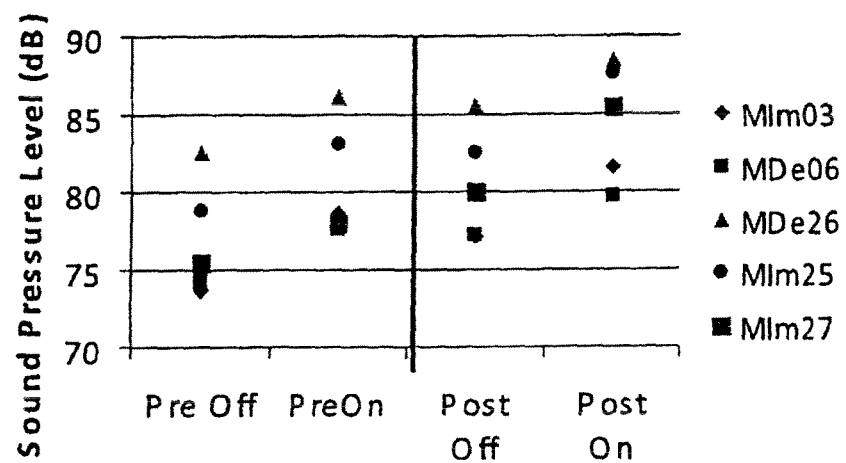
FIGS. 12 and 13 illustrate testing data from Parkinson's Disease patients and the results realized by the patients as a result of wearing the voice enhancement device over a prescribed period of time.
Figure 13:
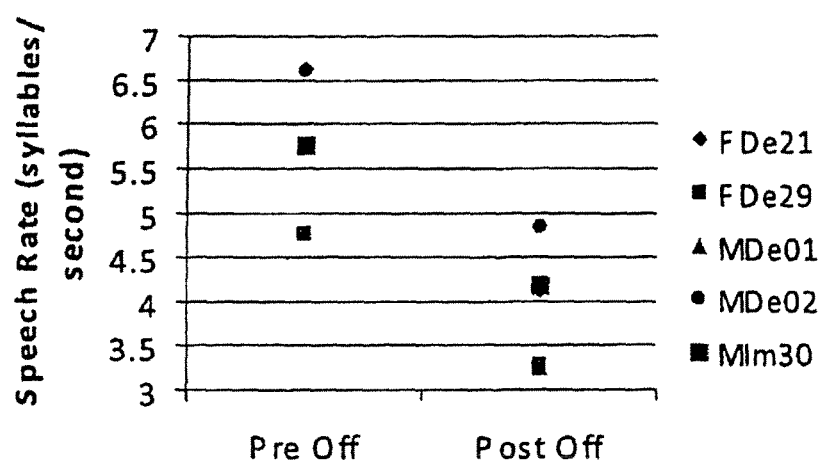

FIGS. 12-13 and discussion below involve testing results from training thirty-six (36) Parkinson's Disease Patients ("PDPs") in a study using the voice enhancement device 10 over an eight (8) week period. The PDPs realized a number of positive changes in their communication as a result of the training and use of the device 10. The positive changes that were realized discussed further below include: increased Sound Pressure Levels and altered Speech Rate.

FIGS. 12-13 relating to the testing results illustrate data taken from one session before the device 10 was positioned on the patient or user is labeled "Pre". The data taken as the end of the eight (8) week training period is labeled "Post". At all data points shown in FIGS. 12-13, the data was measured with the device 10 off (labeled "Off") and then on (labeled "On"). The training consisted of the patients wearing the device in communicative environments for 4-6 hours per day for eight (8) weeks. The PDPs returned every two (2) weeks for evaluation. Testing then occurred with the patients having the device 10 off and on.

Sound Pressure Level

Sound Pressure Level ("SPL") is a measure of the intensity of the voice. PDPs often have weak, quiet voices, making vocal intensity a major therapy target. Referring now to FIG. 12, the SPLs (shown along the vertical axis) were higher with the device 10 on than when the device 10 was off before training due to the Lombard Effect. The SPL data in FIG. 12 was collected from an extemporaneous speech task where PDPs talked about a topic of their choice for two (2) minutes. This task is indicative of real-world speech production.

Unlike the left side of FIG. 12 that illustrates the effects of the device 10 before training, the right side of FIG. 12 demonstrates that the patients continue to increase SPL and loudness when wearing the device after eight (8) weeks of therapy. When comparing the Pre Off and Post Off data of FIG. 12, it illustrates the effects of training (or therapy) with the device 10 over an eight (8) week period. The patients benefited by increasing SPL and loudness, according to the data shown in FIG. 12 even when the patients were not using the device after training.

Speech Rate

Speech Rate is a measure of the number of syllables produced per second. PDPs sometimes speak more quickly than typical speakers, making a reduction in rate one possible therapy target. FIG. 13 illustrates the training effect of the device 10 on speech rate (syllables produced per second). A higher number reflects a faster speech rate.

Speech rate data was collected in FIG. 13 during the study from an extemporaneous speech task where patients talked about a topic of their choice for two (2) minutes. This task is indicative of real-world speech production. As can be seen in FIG. 13, the patients in the study realized a significant change (for the patients depicted in FIG. 13, the change was a decrease) in speech rate after experiencing training for an eight (8) week period with the voice enhancement device 10.

The data of FIG. 13 demonstrate a training effect in that patients are producing a slower speech rate after training even while the device is off. Although not all patients in the study demonstrated a reduction in speech rate and some experience an increase. As well, not all patients in the study demonstrated a large (greater than one (1) syllable per second) change. But, those patients that did demonstrate a large change transitioned toward a more typical rate.

Such changes in speech rate were advantageously experienced for at least two reasons. First, data from the study on the results of the Lombard Effect in individuals with Parkinson's disease have not typically shown a change in rate. Typically, younger and older adults tend to slow their rate when speaking in a noisy or loud environment. Individuals with Parkinson's disease have not typically shown any significant change in rate. However, these data are the first to show the effects of training over eight (8) weeks with the Lombard Effect. Secondly, trained changes in rate during connected speech (as demonstrated above) are rare in speech therapy. No other therapy is known to have been proven to make large changes in rate possible during connected speech. Such large changes in speech rate have been advantageously experienced as a result of the type of training methodologies used and described herein, along with the implementation of such training in connection with the use of the voice enhancement device 10.

Lung Volume Initiation and Lung Volume Termination

Figure 17:
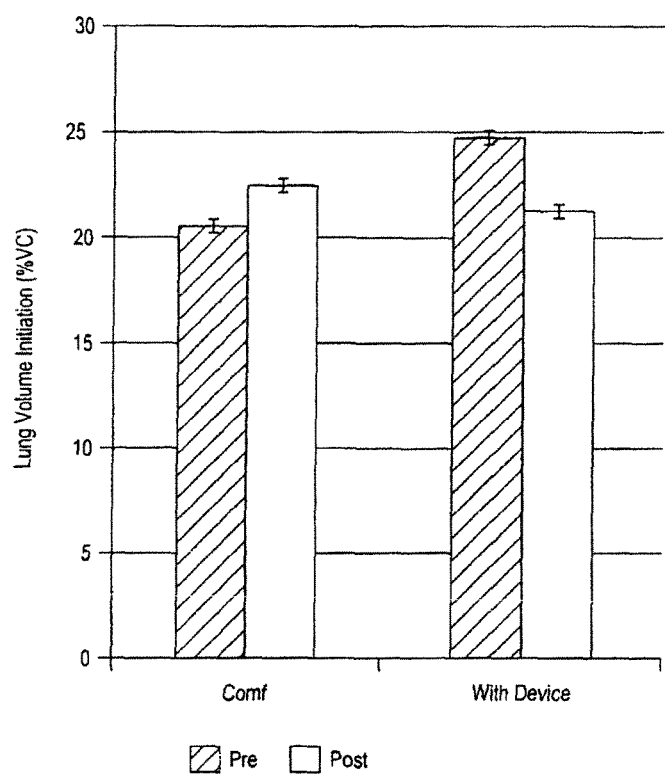
FIGS. 17-18 illustrate testing data from Parkinson's Disease patients and the results realized by the patients as a result of wearing the voice enhancement device over a prescribed period of time.
Figure 18:
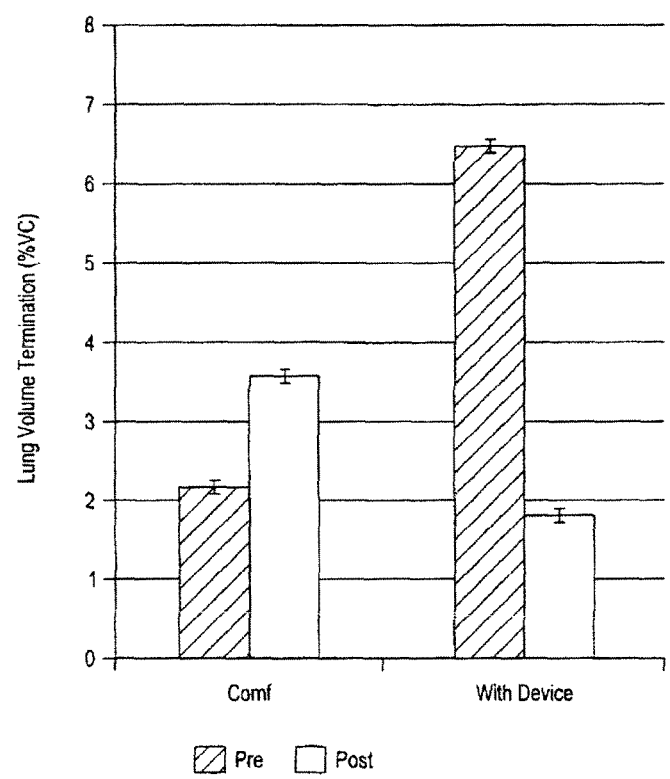

FIGS. 17-18 illustrate testing data from Parkinson's Disease patients and the results realized by the patients as a result of wearing the voice enhancement device 10 over a prescribed period of time. In particular, FIGS. 17-18 illustrate the impact the device 10 has on the patient's respiratory system, namely lung volume initiation and termination.

FIGS. 17-18 and discussion below involve testing results from training thirty-six (36) Parkinson's Disease Patients ("PDPs") in a study using the voice enhancement device 10 over an eight (8) week period. The PDPs realized a number of positive changes in their respiratory system as a result of the training and use of the device 10. The positive changes that were realized discussed further below include: increased lung volume.

FIGS. 17-18 relating to the testing results illustrate data taken from one session before the device 10 was positioned on the patient or user is labeled "Pre". The data taken as the end of the eight (8) week training period is labeled "Post". All data shown in FIGS. 17-18, the data was measured with the device 10 off (labeled "Comf") and then on (labeled "With Device"). The training consisted of the patients wearing the device in communicative environments for 4-6 hours per day for eight (8) weeks. The PDPs returned every two (2) weeks for evaluation. Testing then occurred with the patients having the device 10 off and on.

As illustrated in FIGS. 17 and 18, the measurements of lung volume initiation reflect the amount of air volume in the lungs when the patient begins to talk. Similarly, lung volume termination reflects the amount of air in the lungs when the patient stops talking. These measures can be used to determine the adequacy of respiratory support for speech. Pre-training, using the device and speaking at a higher intensity resulted in patients using much higher lung volume initiations and terminations. This means that patients used greater inspiratory muscle effort to breathe to a higher lung volume before speaking Given the potential for chest wall rigidity in Parkinson's Disease, this is not the most efficient mechanism of support from the respiratory system. However, after training, even though patients were speaking at a higher intensity at comfortable, they only marginally increased their lung volume initiations and terminations. Further increasing vocal intensity by again using the device after training did not result in a change in lung volume initiations and did result in a decrease in lung volume terminations. The post-training response from the PDPs was consistent with patterns seen in typical older adults speaking in noise. This means that respiratory support for speech was more typical in the patients after training.

Methodologies for Use with the Voice Enhancement Device 10

Figure 14:
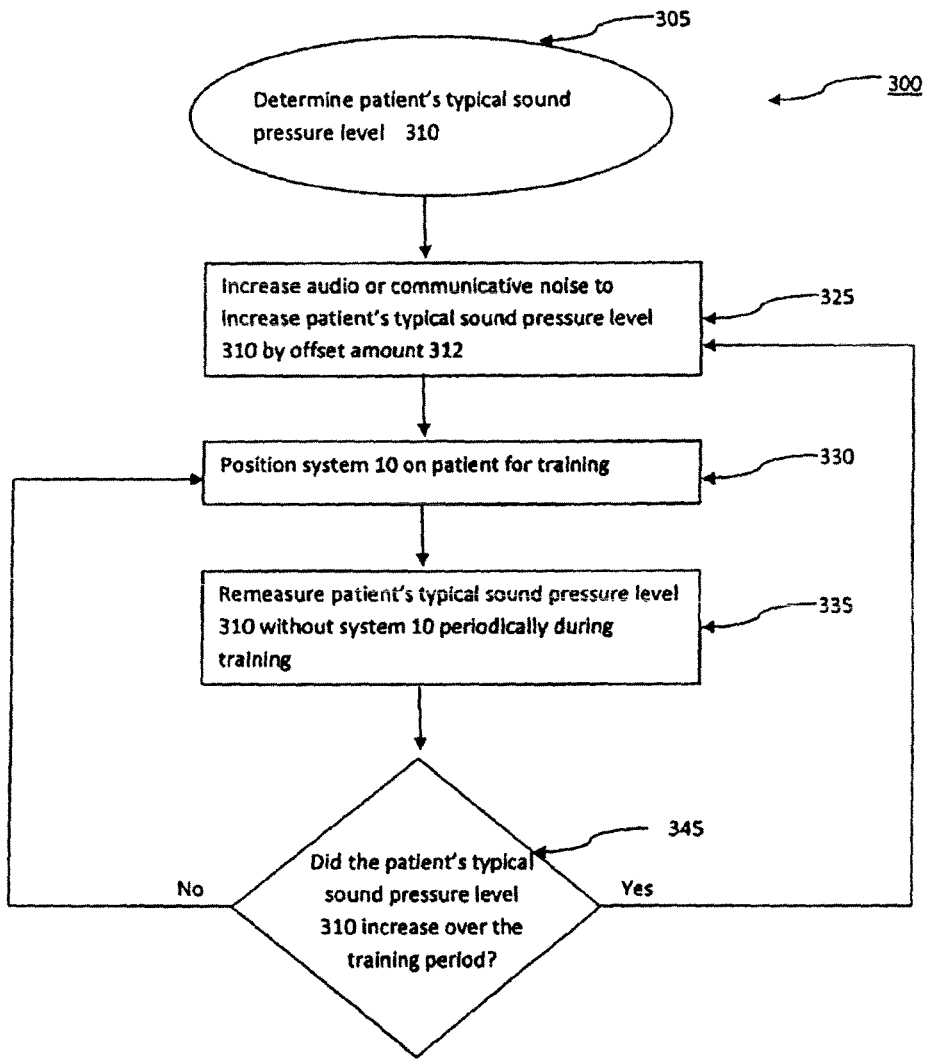
FIG. 14 illustrates one methodology used for training patients using the voice enhancement device in accordance with one example embodiment of the present disclosure.

One methodology 300, illustrated in FIG. 14 used for training patient's with the device 10 in accordance with one exemplary embodiment of the present disclosure comprises interviewing each patient to determine a patient specific pre-training typical sound pressure level 310. A typical sound pressure level 310 is determined by measuring the loudness or sound level projected by each patient during speech while the patient is "off" the device 10. Once the typical sound pressure level 310 (measured in dBAs) is determined, this level 310 is used to set the audio 68 or communicative noise 31 projected from the device 10 to the patient through one or more earpieces 16. A patient's typical sound pressure level for the device 10 is set based on a dialog between medical personnel (such as physicians, nurses, speech-language pathologists etc.) and the patient.

The methodology 300 continues by increasing the audio 68 or communicative noise 31 in the voice enhancement device 10 to an offset amount 312, while the device is positioned on the patient during connected speech. In one example embodiment, the offset amount 312 is approximately five (5) (dBA) higher SPL than the patient's typical sound pressure level 310. In the illustrated example embodiment of FIGS. 1 and 14, the noise is increased in the device 10 by a turn-screw adjustment accessible through the housing 12 by medical personnel. The voice enhancement device 10 is then positioned on the patient for training. In an alternative example embodiment, the noise 31 is increased in the device 10 through an interface using computer readable media such as software.

The methodology 300 further continues by remeasuring the patient's typical sound pressure level 310 every two weeks off the device 10. The device 10 would then be recalibrated to elicit an approximately five (5) (dBA) increase in SPL above the typical SPL 310 during connected speech. The methodology 300 was used to train patients in the study reflected in the data of FIGS. 12 and 13.

Referring again to FIG. 14, the methodology 300 is shown for training patient's using the voice enhancement device 10 in accordance with one exemplary embodiment of the present disclosure. At 305, a pre-training patient's typical sound pressure level 310 is determined for the patient without the device 10. The method proceeds to 325, where the audio 68 or communicative noise 31 is increased to augment the patient's typical sound pressure level 310 by an offset amount 312. At 330, the voice enhancement device 10 is positioned on the patient for training. At 335 the patient's typical sound pressure level 310 is remeasured without the device 10 periodically during training. At 345, a determination is made on whether or not the patient's typical sound pressure level 310 increased over the training period. If the determination at 345 was an affirmative, the methodology 300 returns to step 325, resulting in an increase of the audio or communicative noise to the patient's earpiece 16 by further increasing the output of the device 10 to maintain the offset amount 312. If the determination at 345 was negative, the methodology 300 returns to step 330, resulting in a continuation of the training with the voice enhancement device 10 at the same output level of the noise projected from the device 10 into the one or more earpieces 16 to the patient.

Figure 15:
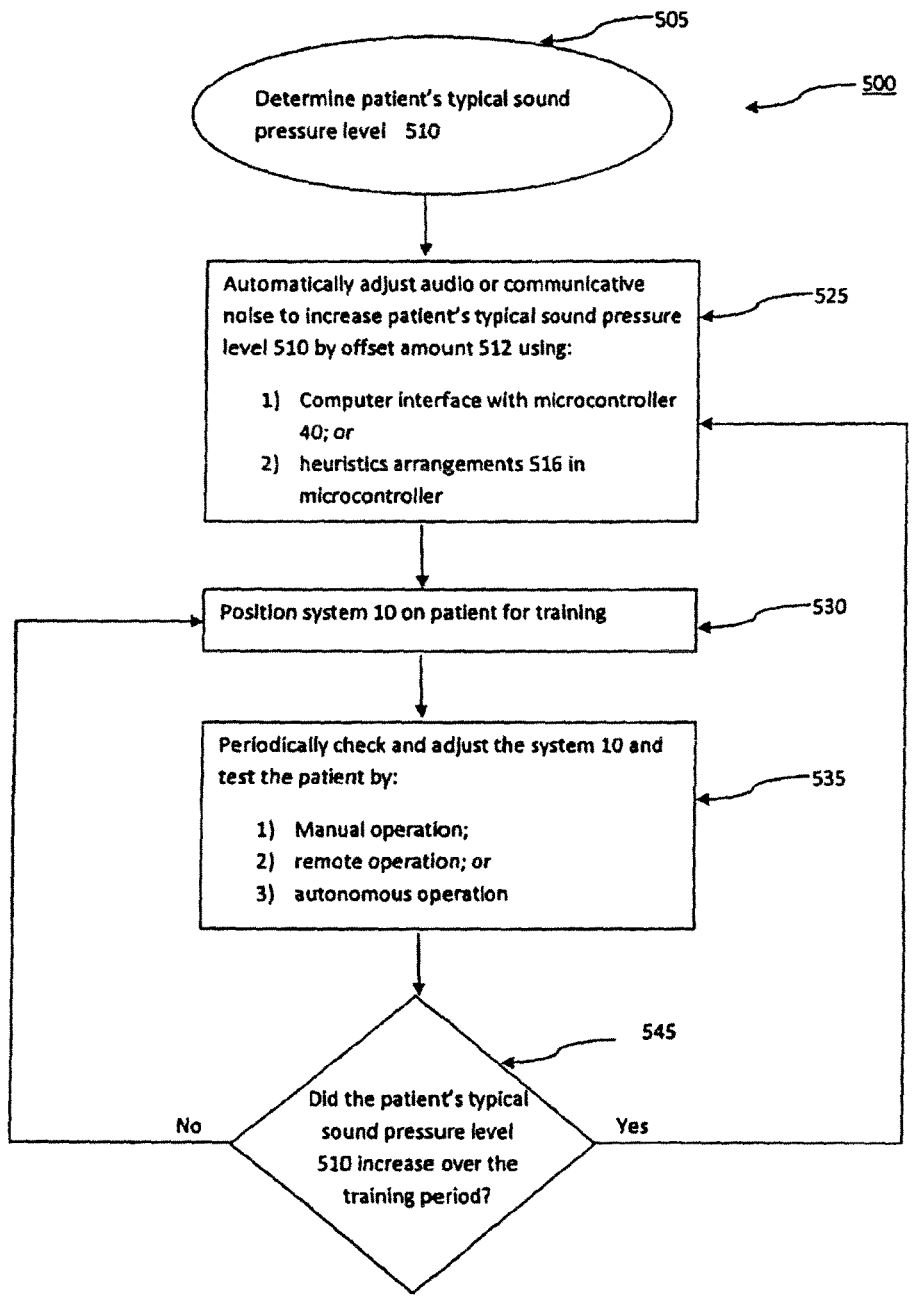
FIG. 15 illustrates another methodology used for training patients using the voice enhancement device in accordance with one example embodiment of the present disclosure.

FIG. 15 illustrates yet another methodology 500 for training patient's using the voice enhancement device 10 in accordance with another exemplary embodiment of the present disclosure. The methodology 500 comprises interviewing each patient to determine each patient's typical sound pressure level 510. Similar to the methodology 300 described above, a patient's typical sound pressure level 510 is established based on a dialog. After the dialog and measurement of the patient's typical sound pressure level 510, the patient is fitted with the device 10.

The methodology 500 continues by increasing the audio 68 or communicative noise 31 in the voice enhancement device 10 to an offset amount 512 using a computer interface in communication with the microcontroller 40 while the device is placed on the patient during connected speech. In one example embodiment, the offset amount 512 is approximately five (5) (dBA) higher SPL than the set pre-training typical sound pressure level 510.

In an alternative example embodiment, software 140 operating the microcontroller 40 of the voice enhancement device 10 includes heuristic arrangements 516 that analyze signatures or characteristics in the patient's speech patterns and/or loudness to alter the offset amount 512 relative to the typical sound pressure level 510. For example, the heuristic arrangements 516 in the device program 140 microcontroller 40 may increase or decrease the offset amount 512 at a prescribed period 518 based on information about the patient or device 10 stored, for example, in patient usage data 88 found in flash memory 142 or micro memory card 70. The prescribed period 518 can be as short as microseconds and as long as weeks.

At set intervals, the methodology 500 further continues allowing the device 10, and more specifically microcontroller 40, to check and adjust the audio 68 or communicative noise 31 projected from the earpiece 16 by increasing the audio or noise (to a safe limit) and testing the patient's response to the increase. Based on the patient's response the audio 68 or communicative noise 31 projected to the earpiece 16 the offset amount 512 may be periodically adjusted by increasing or decreasing for training speech. Such a periodic adjustment to the device 10 may occur manually by medical personnel, remotely from medical personnel through for example, a wireless protocol transmitted to a receiver coupled with the microcontroller 40, autonomously through the heuristic arrangements 516 of the microcontroller 40, or any combination thereof. The methodology 500 further continues by retesting the patient's typical sound pressure level 510 and adjusting the offset amount 512 based on the history of the voice enhancement device 10 and the patient's presentation.

Referring again to FIG. 15, the methodology 500 is shown for training patient's using the voice enhancement device 10 in accordance with one exemplary embodiment of the present disclosure. At 505, a pre-training typical sound pressure level 510 is determined for the patient. The method proceeds to 525, where the audio or communicative noise is increased to an offset amount 512 via a computer interface with the microcontroller 40 or through heuristic arrangements 516 within the microcontroller 40. At 530, the device 10 is positioned on the patient for training. At 535, a periodic check, and adjustment of the device 10 occurs along with a testing of the patient, all of which occur by manual operation, remote operation, and/or autonomous operation. At 545, a determination is made on whether or not the patient's typical sound pressure level 510 increased over the training period. If the determination at 545 was an affirmative, the methodology 500 returns to step 525, resulting in an increase of the audio or communicative noise to the patient's earpiece 16 by further increasing the output of the device 10 to maintain the offset amount 512. If the determination at 545 was negative, the methodology 500 returns to step 530, resulting in a continuation of the training with the voice enhancement device 10 at the same output level of the noise projected from the device into the one or more earpieces 16 to the patient.

The present technology provides a number of advantages including providing a voice enhancement device that provides a source of multitalker babble to a user's ear through an earpiece during the user's speech, resulting in several positive and trained conditions in the patient, including increased sound pressure levels, normalized speech rate, improved respiratory support, and improved articulation. The earpiece advantageously incorporates an accelerometer located with the earpiece to detect the user's speech based on vocal fold vibrations that resonate near the user's ear canal. This provides a more compact, discreet device for providing the described voice enhancement benefits.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A voice enhancement device comprising:
an earpiece configured to be positioned in an ear canal of a user;
a microcontroller operatively coupled to the earpiece;
an accelerometer located within the earpiece and operatively coupled to the microcontroller, wherein the accelerometer is configured to detect speech by the user and provide an output signal to the microcontroller, wherein the microcontroller has at least a first state in which multitalker babble is retrieved and provided to the earpiece in response to the received output signal from the accelerometer when the received output signal is above a reference level configured to indicate detected speech by the user, wherein the multitalker babble is retrieved and provided to the earpiece at all levels of detected speech by the user, and a second state without the retrieval and provision of the multitalker babble when the received output signal is below the reference level indicating an absence of detected speech by the user.

2. The device of claim 1, wherein an amplitude of the multitalker babble is adjustable.

3. The device of claim 1, wherein the earpiece comprises a non-occlusive ear fitting.

4. The device of claim 1, wherein the accelerometer provides the output signal to the microcontroller based on a detected movement of the accelerometer.

5. The device of claim 4, wherein the detected movement of the accelerometer is in response to vocal fold vibrations of the user that resonate near the ear canal.

6. The device of claim 4, wherein the microcontroller further comprises a comparator having a set threshold and wherein the microcontroller provides the multitalker babble to the earpiece when the output signal is above the threshold.

7. The device of claim 6, wherein the microcontroller provides the multitalker babble to the earpiece until the output signal drops below the threshold.

8. The device of claim 6, wherein the multitalker babble continues for a set period of time after the output signal drops below the threshold.

9. The device of claim 1, further comprising a memory coupled to the microcontroller, wherein the microcontroller is configured to store data in the memory relating to when the multitalker babble is provided to the earpiece.

10. A method of making a voice enhancement device comprising:
providing an earpiece configured to be positioned in an ear canal of a user;
operatively coupling a microcontroller to the earpiece;
operatively coupling an accelerometer located in the earpiece to the microcontroller, wherein the accelerometer is configured to detect speech by the user and provide an output signal to the microcontroller, wherein the microcontroller has at least a first state in which multitalker babble is retrieved and provided to the earpiece in response to the received output signal from the accelerometer when the received output signal is above a reference level configured to indicate detected speech by the user, wherein the multitalker babble is retrieved and provided to the earpiece at all levels of detected speech by the user, and a second state without the retrieval and provision of the multitalker babble when the received output signal is below the reference level indicating an absence of detected speech by the user.

11. The method of claim 10, wherein an amplitude of the provided multitalker babble is adjustable.

12. The method of claim 10, wherein the earpiece comprises a non-occlusive ear fitting.

13. The method of claim 10, wherein the accelerometer provides the output signal to the microcontroller based on a detected movement of the accelerometer.

14. The method of claim 13, wherein the detected movement of the accelerometer is in response to vocal fold vibrations of the user that resonate near the ear canal.

15. The method of claim 13, wherein the microcontroller further comprises a comparator having a set threshold and wherein the microcontroller provides the multitalker babble to the earpiece when the output signal is above the threshold.

16. The method of claim 15, wherein the microcontroller provides the multitalker babble to the earpiece until the output signal drops below the threshold.

17. The method of claim 15, wherein the multitalker babble continues for a set period of time after the output signal drops below the threshold.

18. The method of claim 10, further comprising:
coupling a memory coupled to the microcontroller, wherein the microcontroller is configured store data in the memory relating to when the multitalker babble is provided to the earpiece.

19. A method for increasing vocal loudness in a patient, the method comprising:
positioning an earpiece comprising an accelerometer in an ear canal of the patient;
providing a microcontroller operatively coupled to the earpiece wherein the accelerometer is configured to detect speech by the user and provide an output signal to the microcontroller, wherein the microcontroller has at least a first state in which multitalker babble is retrieved and provided to the earpiece in response to the received output signal from the accelerometer when the received output signal is above a reference level configured to indicate detected speech by the user, wherein the multitalker babble is retrieved and provided to the earpiece at all levels of detected speech by the user, and a second state without the retrieval and provision of the multitalker babble when the received output signal is below the reference level indicating an absence of detected speech by the user.

20. The method of claim 19, wherein an amplitude of the provided multitalker babble is adjustable.

21. The method of claim 19, wherein the earpiece comprises a non-occlusive ear fitting.

22. The method of claim 21, further comprising a memory coupled to the microcontroller, wherein the microcontroller is configured to store data in the memory relating to when the multitalker babble is provided to the earpiece.

23. The method of claim 19, wherein the accelerometer provides the output signal to the microcontroller based on a detected movement of the accelerometer.

24. The method of claim 23, wherein the detected movement of the accelerometer is in response to vocal fold vibrations of the user that resonate near the ear canal.

25. The method of claim 23, wherein the microcontroller further comprises a comparator having a set threshold and wherein the microcontroller provides the multitalker babble to the earpiece when the output signal is above the threshold.

26. The method of claim 25, wherein the microcontroller provides the multitalker babble to the earpiece until the output signal drops below the threshold.

27. The method of claim 25, wherein, the multitalker babble continues for a set period of time after the output signal drops below the threshold.

* * * * *